(12) United States Patent
McNeel

(10) Patent No.: US 7,179,797 B2
(45) Date of Patent: Feb. 20, 2007

(54) METHODS AND COMPOSITIONS FOR TREATING PROSTATE CANCER USING DNA VACCINES

(75) Inventor: Douglas McNeel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/669,474

(22) Filed: Sep. 25, 2003

(65) Prior Publication Data

US 2004/0142890 A1   Jul. 22, 2004

Related U.S. Application Data

(60) Provisional application No. 60/413,777, filed on Sep. 27, 2002.

(51) Int. Cl.
 A61K 48/00   (2006.01)
 C12N 15/11   (2006.01)
(52) U.S. Cl. ........................................ 514/44; 536/23.1
(58) Field of Classification Search ............... 536/23.1; 514/44; 435/320.1, 325, 455
 See application file for complete search history.

(56) References Cited

U.S. PATENT DOCUMENTS 5,925,362 A * 7/1999 Spitler et al. ............. 424/277.1
6,328,969 B1 * 12/2001 Houghton et al. ....... 424/184.1

OTHER PUBLICATIONS

Verma et al., Gene therapy-promises, problems and prospects. (1997) Nature. 389:239-242.*
Orkin et al., Report and Reccommendations of the Panel to assess the NIH invextment in Research on Gene Therapy (1998) 1-41.*
Marshall., Gene Therapy's Growing Pains (1995) Science 269:1050-1055.*
Rosenberg et al. (2003) Inability to Immunize Patients with Metastatic Melanoma Using Plasmid DNA Encoding the gp100 Melanoma-Melanocyte Antigen. 14:709-714.*
McCluskie et al. (1999) Route and method of DNA vaccine influence immune responses in mice and non-human primates. Mol. Med. 5:287-300.*
Hu et al. (1998) Gene-Modified Tumor Vaccine with Therapeutic Potential Shifts Tumor-Specific T cell Response from a Type 2 to a Type 1 Cytokine Profile. J. Immunol. 161:3033-3041.*
Acsadi G. Jiao SS. Jani A. Duke D. Williams P. Chong W. Wolff JA. Direct gene transfer and expression into rat Heart in vivo. [Journal Article] *New Biologist.* 3(1):71-81, Jan. 1991.
Boyer JD. Cohen AD. Vogt S. Schumann K. Nath B. Ahn L. Lacy K. Bagarazzi ML. Higgins TJ. Baine Y. Ciccarelli RB. Ginsberg RS. MacGregor RR. Weiner DB. Vaccination of seronegative volunteers with a human immunodeficiency virus type 1 env/rev DNA vaccine induces antigen-specific proliferation and lymphocyte production of beta-chemokines. [Clinical Trial. Clinical Trial, Phase I, Journal Article] *Journal of Infectious Diseases.* 181(2): 476-83, Feb. 2000.
Budker V. Zhang G. Knechtle S. Wolff JA. Naked DNA delivered intraportally expresses efficiently in hepatocytes. [Journal Article] *Gene Therapy.* 3(7):593-8, Jul. 1996.
Budker V. Gurevich V. Hagstrom JE. Bortzov F. Wolff JA. pH-sensitive, cationic liposomes: a new synthetic virus-like vector. [Journal Article] *Nature Biotechnology.* 14(6):760-4, Jun. 1996.
Budker V. Zhang G. Danko I. Williams P. Wolff J. The efficient expression of intravascularly delivered DNA in rat muscle. [Journal Article] *Gene Therapy.* 5(2):272-6, Feb.1998.
Burch PA. Breen JK. Buckner JC. Gastineau DA. Kaur JA. Laus RL. Padley DJ. Peshwa MV. Pitot HC. Richardson RL. Smits BJ. Sopapan P. Strang G. Valone FH. Vuk-Pavlovic S. Priming tissue-specific cellular immunity in a phase I trial of autologous dendritic cells for prostate cancer. [Clinical Trial. Clinical Trial, Phase I. Journal Article] *Clinical Cancer Research.* 6(6):2175-82, Jun. 2000.
Cadeddu JA. Partin AW. Epstein JI. Walsh PC. Stage D1 (T1-3, N1-3, M0) prostate cancer: a case-controlled comparison of conservative treatment versus radical prostatectomy. [Journal Article] *Urology.* 50(2):251-5, Aug. 1997.
Chen Y. Webster RG. Woodland DL. Induction of CD8+ T cell responses to dominant and subdominant epitopes and protective immunity to Sendai virus infection by DNA vaccination. [Journal Article] *Journal of Immunology.* 160(5):2425-32, Mar. 1, 1998.
Cho HJ. Takabayashi K. Cheng PM. Nguyen MD. Corr M. Tuck S. Raz E. Immunostimulatory DNA-based vaccines induce cytotoxic lymphocyte activity by a T-helper cell-independent mechanism. [comment]. [Journal Article] *Nature Biotechnology.* 18(5):509-14, May 2000.
Danko I. Fritz JD. Jiao S. Hogan K. Latendresse JS. Wolff JA. Pharmacological enhancement of in vivo foreign gene expression in muscle. [Journal Article] *Gene Therapy.* 1(2):114-21, Mar. 1994.
Davis HL. Whalen RG. Demeneix BA. Direct gene transfer into skeletal muscle in vivo: factors affecting efficiency of transfer and stability of expression. [Journal Article] *Human Gene Therapy.* 4(2):151-9, Apr. 1993.

(Continued)

*Primary Examiner*—Anne-Marie Falk
*Assistant Examiner*—Louis D. Lieto
(74) *Attorney, Agent, or Firm*—Quarles & Brady, LLP

(57) ABSTRACT

A DNA vaccine for the treatment of prostate cancer, comprising a plasmid vector comprising a nucleotide sequence encoding prostatic acid phosphatase (PAP) operably linked to a transcription regulatory element, wherein upon administration to a mammal a cytotoxic immune reaction against cells expressing PAP is induced. In preferred embodiment, the PAP encoded is a xenoantigen highly homologous to the autoantigen PAP of the mammal. Also disclosed are methods for inducing prostatitis, or inducing immune reaction to PAP, or treating prostate cancer in a mammal, using the DNA vaccine and pharmaceutical compositions comprising the vaccine. Preferably, xenoantigen vaccination is followed by boosting with autoantigen PAP from the same animal species as the mammal being treated.

6 Claims, 23 Drawing Sheets

OTHER PUBLICATIONS

Fong L. Ruegg CL. Brockstedt D. Engleman EG. Laus R. Induction of tissue-specific autoimmune prostatitis with prostatic acid phosphatase immunization: implications for immunotherapy of prostate cancer. [Journal Article] *Journal of Immunology.* 159(7):3113-7, Oct. 1, 1997.

Fong L. Brockstedt D. Benike C. Breen JK. Strang G. Ruegg CL. Engleman EG. Dendritic cell-based xenoantigen vaccination for prostate cancer immunotherapy. [Clinical Trial. Clinical Trial, Phase I. Journal Article] *Journal of Immunology.* 167(12):7150-6, Dec. 15, 2001.

Guinan P. Ray P. Shaw M. Immunotherapy of prostate cancer: a review. [Review] [57 refs ] [Clinical Trial. Journal Article. Review] *Prostate.* 5(2):221-30, 1984.

Hartmann G. Weeratna RD. Ballas ZK. Payette P. Blackwell S. Suparto I. Rasmussen WL. Waldschmidt M. Sajuthi D. Purcell RH. Davis HL. Krieg AM. Delineation of a CpG phosphorothioate oligodeoxynucleotide for activating primate immune responses in vitro and in vivo. [Journal Article] *Journal of Immunology.* 164(3):1617-24, Feb. 1, 2000.

Irvine KR. Restifo NP. The next wave of recombinant and synthetic anticancer vaccines. [Review] [121 refs] [Journal Article. Review. Review, Tutorial] *Seminars in Cancer Biology.* 6(6):337-47, Dec. 1995.

Iwasaki A. Torres CA. Ohashi PS. Robinson HL. Barber BH. The dominant role of bone marrow-derived cells in CTL induction following plasmid DNA immunization at different sites. [Journal Article] *Journal of Immunology.* 159(1):11-4, Jul. 1, 1997.

Lebowitz MS. O'Herrin SM. Hamad AR. Fahmy T. Marguet D. Barnes NC. Pardoll D. Bieler JG. Schnech JP. Soluble, high-affinity dimers T-cell receptors and class II major histocompatibility complexes: biochemical probes for analysis and modulation of immune responses. [Journal Article] *Cellular Immunology.* 192(2):175-84, Mar. 15, 1999.

Lee Ah. Suh YS. Sung. JH. Yang SH. Sung YC. Comparison of various expression plasmids for the induction of immune response by DNA immunization. [Journal Article] *Molecules & Cells.* 7(4):495-501, Aug. 31, 1997.

Mahi-Brown CA. McGuinness RP. Moran F. The cellular immune response to immunization with zona pellucida antigens. [Journal Article] *Journal of Reproductive Immunology.* 21(1):29-46, Jan. 1992.

Mahi-Brown CA. Primate response to immunization with a homologous zona pellucida peptide. [Journal Article] *Journal of Reproduction & Fertility—Supplement.* 50:165-74, 1996.

Manthorpe M. Comefert-Jensen F. Hartikka J. Felgner J. Rundell A. Margalith M. Dwarki V. Gene therapy by intramuscular injection of plasmid DNA: studies on firefly luciferase gene expression in mice. [Journal Article] *Human Gene Therapy.* 4(4):419-31, Aug. 1993.

McNeel DG. Schiffman K. Disis ML. Immunization with recombinant human granulocyte-macrophage colony-stimulating factor as a vaccine adjuvant elicits both a cellular and humoral response to recombinant human granulocyte-macrophage colony-stimulating factor. [Clinical Trial. Clinical Trial, Phase I. Journal Article] *Blood.* 93(8):2653-9, Apr. 15, 1999.

McNeel DG. Nguyen LD. Storer BE. Vessella R. Lange PH. Disis ML. Antibody immunity to prostate cancer associated antigens can be detected in the serum of patients with prostate cancer. [Journal Article] *Journal of Urology.* 164(5):1825-9, Nov. 2000.

McNeel DG. Disis ML. Tumor vaccines for the management of prostate cancer. [Review] [63 refs] [Journal Article. Review. Review, Tutorial] *Archivum Immunologiae et Therapiae Experimentalis.* 48(2):85-93, 2000.

McNeel DG. Nguyen LD. Disis ML. Identification of T helper epitopes from prostatic acid phosphatase. [Journal Article] *Cancer Research.* 61(13):5161-7, Jul. 1, 2001.

McNeel DG. Nguyen LD. Ellis WJ. Higano CS. Lange PH. Disis ML. Naturally occurring prostate cancer antigen-specific T cell responses of a Th1 phenotype can be detected in patients with prostate cancer. [Journal Article] *Prostate.* 47(3):222-9, May 15, 2001.

Mincheff M. Tchakarov S. Zoubak S. Loukinov D. Botev C. Altankova I. Georgiev G. Petrov S. Meryman HT. Naked DNA and adenoviral immunizations for immunotherapy of prostate cancer: a phase I/II clinical trial. [Clinical Trial. Clinical Trial, Phase I. Clinical Trial, Phase II. Journal Article] *European Urology,* 38(2):208-17, Aug. 2000.

Murphy GP. Tjoa BA. Simmons SJ. Ragde H. Rogers M. Elgamal A. Kenny GM. Troychak MJ. Salgaller ML. Boynton AL. Phase II prostate cancer vaccine trial: report of a study involving 37 patients with disease recurrence following primary treatment. [Clinical Trial. Clinical Trial, Phase II. Journal Article] *Prostate.* 39(1):54-9, Apr. 1, 1999.

O'Brien K. Cokkinides V. Jemal A. Cardinez CJ. Murray T. Samuels A. Wards E. Thun MJ. Cancer statistics for Hispanics, 2003. [Journal Article] *Ca: a Cancer Journal for Clinician.* 53(4):208-26, Jul.-Aug. 2003.

Oefelein MG. Smith ND. Grayhack JT. Schaeffer AJ. McVary KT. Long-term results of radical retropubic prostatectomy in men with high grade carcinoma of the protate.[comment]. [Journal Article ] *Journal of Urology.158:*(4)1460-5, Oct. 1, 1997.

Oldstone MB. Molecular mimicry and immune-mediated diseases. [Review] [102 refs] [Journal Article. Review. Review, Tutorial] *FASEB Journal.* 12(13):1255-65, Oct. 1998.

Peyton DK. Ramesh T. Spear BT. Position-dependent activity of alpha -fetoprotein enhancer element III in the adult liver is due to negative regulation. [Journal Article] *Proceedings of the National Academy of Sciences of the United States of America.* 97(20):10890-4, Sep. 26, 2000.

Pound CR. Partin AW. Eisenberger MA. Chan DW. Pearson JD. Walsh PC. Natural history of progression after PSA elevation following radical prostatectomy.[comment]. [Journal Article] *JAMA.* 281(17):1591-7, May 5, 1999.

Raz E. Carson DA. Parker SE. Parr TB. Abai AM. Aichinger G. Gromkowski SH. Singh M. Lew D. Yankauckas MA. et al. Intradermal gene immunization: the possible role of DNA uptake in the induction of cellular immunity to viruses. [Journal Article] *Proceedings of the National Academy of Sciences of the United States of America.* 91(20):9519-23, Sep. 27, 1994.

Sanda MG. Smith DC. Charles LG. Hwang C. Pienta KJ. Schlom J. Milenic D. Panicali D. Montie JE. Recombinant vaccinia-PSA (PROSTVAC) can induce a prostate-specific immune response in androgen-modulated human prostate cancer. [Journal Article] *Urology.* 53(2):260-6, Feb. 1999.

Sgrignoli AR. Walsh PC. Steinberg GD. Steiner MS. Epstein JI. Prognostic factors in men with stage D1 prostate cancer: identification of patients less likely to have prolonged survival after radical prostatectomy.[comment]. [Journal Article] *Journal of Urology.* 152(4):1077-81, Oct. 1994.

Siddall JK. Cooper EH. Newling DW. Robinson MR. Whelan P. An evaluation of the immunochemical measurement of prostatic acid phosphatase and prostatic antigen in carcinoma of the prostate. [Journal Article] *European Urology.* 12(2):123-30, 1986.

Small EJ. Fratesi P. Reese DM. Strang G. Laus R. Peshwa MV. Valone FH. Immunotherapy of hormone-refractory prostate cancer with antigen-loaded dendritic cells.[comment]. [Clinical Trial. Clinical Trial, Phase I. Clinical Trial, Phase II. Journal Article] *Journal of Clinical Oncology.* 18(23):3894-903, Dec. 1, 2000.

Tang DC. DeVit M. Johnston SA. Genetic immunization is a simple method for eliciting an immune response. [Journal Article] *Nature.* 356(6365):152-4, Mar. 12, 1992.

Thomson SA. Sherritt MA. Medveczky J. Elliott SL. Moss DJ. Fernando GJ. Brown LE. Suhrbrier A. Delivery of multiple CD8 cytotoxic T cell epitopes by DNA vaccination. [Journal Article] *Journal of Immunology.* 160(4):1717-23, Feb. 15, 1998.

Tighe H. Corr M. Roman M. Raz E. Gene vaccination: plasmid DNA is more than just a blueprint. [Review] [111 refs] [Journal Article. Review. Review, Academic] *Immunology Today.* 19(2):89-97, Feb. 1998.

True LD. Berger RE. Rothman I. Ross SO. Krieger JN. Prostate histopathology and the chronic prostatitis/chronic pelvic pain syndrome: a prospective biopsy study.[comment]. [Journal Article] *Journal of Urology.* 162(6):2014-8, Dec. 1999.

von Herrath MG. Oldstone MB. Virus-induced autoimmune disease. [Review] [73 refs] [Journal Article. Review. Review, Tutorial] *Current Opinion in Immunology.* 8(6):878-85, Dec. 1996.

Wang B. Ugen KE. Srikantan V. Agadjanyan MG. Dang K. Refaeli Y. Sato AI. Boyer J. Williams WV. Weiner DB. Gene inoculation generates immune responses against human immunodeficiency virus type 1. [Journal Article] *Proceedings of the National Academy of Sciences of the United States of America.* 90(9):4156-60, May 1, 1993.

Wolff JA. Malone RW. Williams P. Chong W. Acsadi G. Jani A. Felgner PL. Direct gene transfer into mouse muscle in vivo. [Journal Article] *Science.* 247(4949 Pt 1):1465-8, Mar. 23, 1990.

Wolff JA. Williams P. Acsadi G. Jiao S. Jani A. Chong W. Conditions affecting direct gene transfer into rodent muscle in vivo. [Journal Article] *Biotechniques.* 11(4):474-85, Oct. 1991.

Zhang G. Budker V. Williams P. Subbotin V. Wolff JA. Efficient expression of naked dna delivered intraarterially to limb muscles of nonhuman primates. [Journal Article] *Human Gene Therapy.* 12(4):427-38, Mar. 1, 2001.

Zhang G. Vargo D. Budker V. Armstrong N. Knechtle S. Wolff JA. Expression of naked plasmid DNA injected into the afferent anf efferent vessels of rodent and dog livers.[comment]. [Journal Article] *Human Gene Therapy.* 8(15):1763-72, Oct. 10, 1997.

Zou LP. Ma DH. Levi M. Wahren B. Wei L. Mix E. van der Meide PH. Link H. Zhu J. Antigen-specific immunosuppression: nasal tolerance to P0 protein peptides for the prevention and treatment of experimental autoimmune neuritis in Lewis rats. [Journal Article] *Journal of Neuroimmunology.* 94(1-2):109-21, Feb. 1, 1999.

* cited by examiner

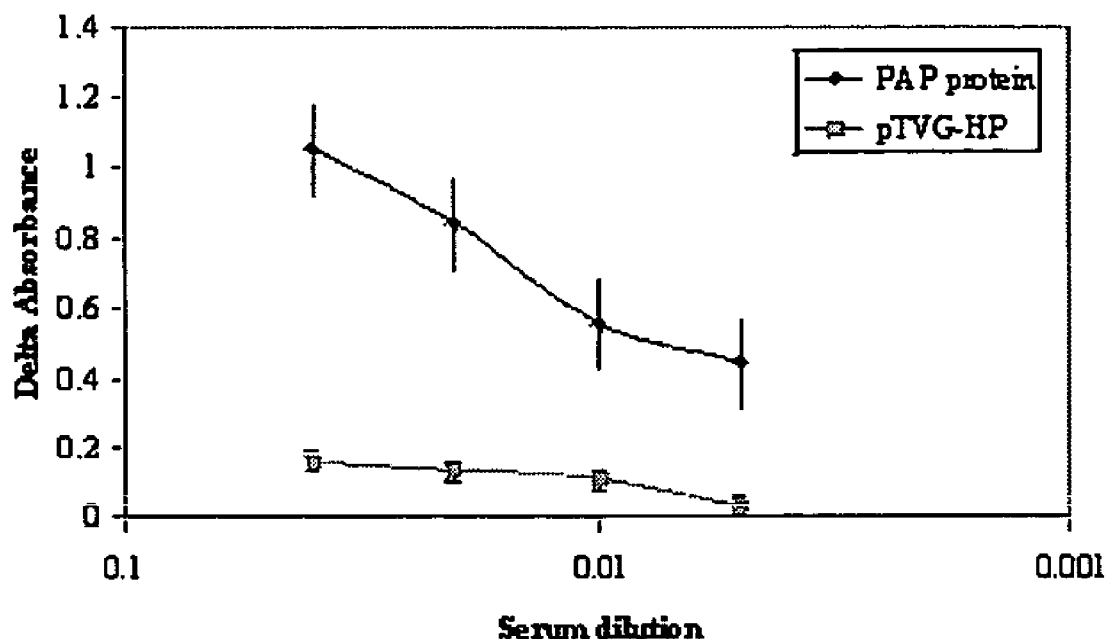
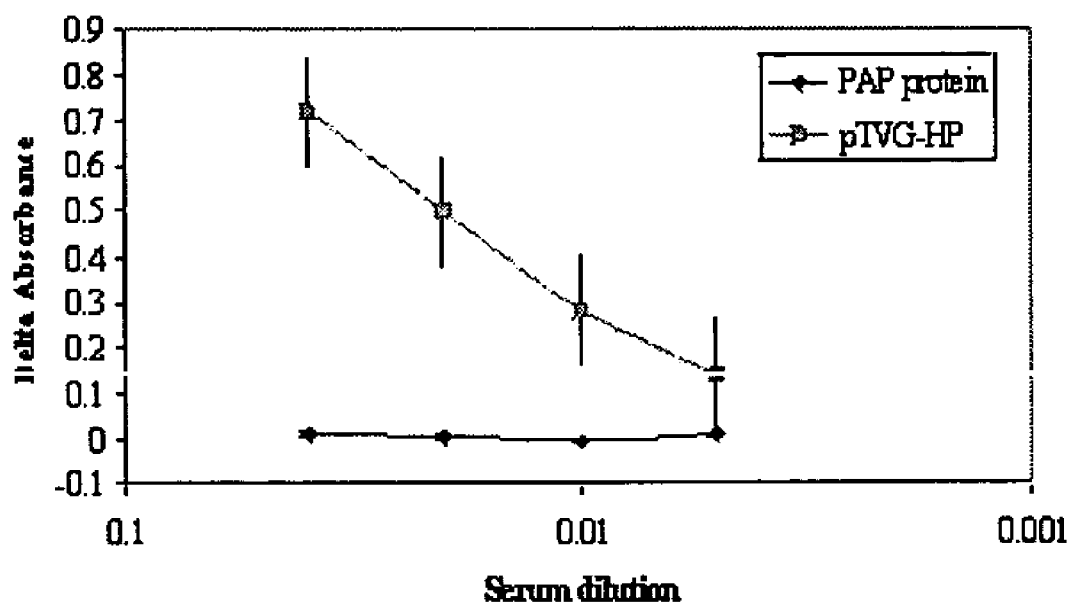
Figure 13

 
Figure 15

Comparison of Human, Rat, and Mouse
Prostatic Acid Phosphatase Amino Acid Sequences

```
  1    MRAVPLPLSR TASLSLGFLL LLSLCLDPGQ .AKELKFVTL VFRHGDRGPI ETFPTDPITE
       |||:|| | |  |||||||||: || : ||    |||||||||| ||||||| || :||||||| |
  1    MRAAPLLLAR AASLSLGFLF LLFFWLDRSV LAKELKFVTL VFRHGDRSPI DTFPTDPIKE
       |||:|| |:   |||:||||: || : ||    |||||||||| ||||||| || :||| |||||
  1    MRAVPLHLVG TASLTLGFLL LLSLRLDPGQ .AKELKFVTL VFRHGDRGPI ETFPNDPIKE

60    SSWPQGFGQL TQWGMEQHYE LGSYIRKRYG RFLNDTYKHD QIYIRSTDVD RTLMSAMTNL
       |||||||||| || |||||||| || ||||||  :|||::|||: |:|||||||| ||||||||||
 61    SSWPQGFGQL TQLGMEQHYE LGEYIRKRYR KFLNESYKHE QVYIRSTDVD RTLMSAMTNL
       |||||||||| |  || |||| || |||:||  :||| ||||: |||||||||| ||||||||||
 60    SSWPQGFGQL TKWGMGQHYE LGSYIRRRYG RFLNNSYKHD QVYIRSTDVD RTLMSAMTNL

120    AALFPPEGIS IWNPRLLWQP IPVHTVSLSE DRLLYLPFRD CPRFEELKSE TLESEEFLKR
       |||||||:| |||| ||||| |||||| ||| | |||||||  |||| || || || |||| ||
121    AALFPPEGVS IWNPILLWQP IPVHTVPLSE DQLLYLPFRN CPRFQELESE TLKSEEFQKR
       |||||||:| |||| ||||| |||||| ||| | |||||||  ||||||| || ||||||| ||
120    AALFPPEGIS IWNPRLLWQP IPVHTVSLSE DRLLYLPFRD CPRFQELKSE TLKSEEFLKR

180    LHPYKSFLDT LSSLSGFDDQ DLFGIWSKVY DPLFCESVHN FTLPSWATED AMIKLKELSE
       |||| |: | |  |||: | |||||||||| |||:|||||| ||||||||||  | ||:||||
181    LHPYKDFIAT LGKLSGLHGQ DLFGIWSKVY DPLYCESVHN FTLPSWATED TMTKLRELSE
       |:||| || | |  |||: | ||| |||::| |||||||||| ||: :||||| |||:||||
180    LQPYKSFIDT LPSLSGFEDQ DLFEIWSRLY DPLYCESVHN FTFRTWATED AMTKLKELSE

240    LSLLSLYGIH KQKEKSRLQG GVLVNEILKN MKLATQPQKY KKLVMYSAHD TTVSGLQMAL
       ||||||||||| ||||||||| |||||||::  || |||    |||:|||||| ||||||||||
241    LSLLSLYGIH KQKEKSRLQG GVLVNEILNH MKRATQIPSY KKLIMYSAHD TTVSGLQMAL
       ||||||||||| ||||||||| ||||||||::  || |||    :||||| | ||||||||||
240    LSLLSLYGIH KQKEKSRLQG GVLVNEILKN MKLATQPQKA RKLIMYSAYD TTVSGLQMAL

300    DVYNGVLPPY ASCHMMELYH DKGGHFVEMY YRNETQNEPY PLTLPGCTHS CPLEKFAELL
       |||||:|||| ||||: |||  :|| ||||| ||||||:||| || ||||: | ||||:||||:
301    DVYNGLLPPY ASCHLTELYF EKGEYFVEMY YRNETQHEPY PLMLPGCSPS CPLERFAELV
       ::|||||||| ||||: |||  ::| :||||| ||||||:||| || ||||: | ||||:|||||
300    ELYNGLLPPY ASCHIMELYQ DNGGTFVEMY YRNETQNEPY PLTLPGCTHS CPLEKFAELL

360    DPVISQDWAT ECMATSSHQG RN        (mouse)        81.6% identical
       ||| ||| |  ||| | ||||                         87.9% homologous
361    GPVIPQDWST ECMTTNSHQG TEDSTD    (human)
       ||||||| |  ||| | || |
360    DPVIPQDWAT ECMGTSNHQA SL        (rat)          79.8% identical
                                                     87.4% homologous
```

Figure 19

SEQUENCE LISTING

```
<160> NUMBER OF SEQ ID NOS: 3

<210> SEQ ID NO 1
<211> LENGTH: 386
<212> TYPE: PRT
<213> ORGANISM: Homo sapiens

<400> SEQUENCE: 1

Met Arg Ala Ala Pro Leu Leu Leu Ala Arg Ala Ala Ser Leu Ser Leu
1               5                   10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110
```

Leu Met Ser Ala Met Thr Asn Leu Ala Ala Leu Phe Pro Pro Glu Gly
            115                 120                 125

Val Ser Ile Trp Asn Pro Ile Leu Leu Trp Gln Pro Ile Pro Val His
        130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Gly Thr Glu Asp Ser
    370                 375                 380

Thr Asp
385

<210> SEQ ID NO 2
<211> LENGTH: 381
<212> TYPE: PRT
<213> ORGANISM: Mus musculus

<400> SEQUENCE: 2

Met Arg Ala Val Pro Leu Pro Leu Ser Arg Thr Ala Ser Leu Ser Leu
1               5                   10                  15

Gly Phe Leu Leu Leu Leu Ser Leu Cys Leu Asp Pro Gly Gln Ala Lys
            20                  25                  30

Glu Leu Lys Phe Val Thr Leu Val Phe Arg His Gly Asp Arg Gly Pro
        35                  40                  45

Ile Glu Thr Phe Pro Thr Asp Pro Ile Thr Glu Ser Ser Trp Pro Gln
    50                  55                  60

Gly Phe Gly Gln Leu Thr Gln Trp Gly Met Glu Gln His Tyr Glu Leu
65                  70                  75                  80

Gly Ser Tyr Ile Arg Lys Arg Tyr Gly Arg Phe Leu Asn Asp Thr Tyr

-continued

```
                85                  90                  95
Lys His Asp Gln Ile Tyr Ile Arg Ser Thr Asp Val Asp Arg Thr Leu
            100                 105                 110
Met Ser Ala Met Thr Asn Leu Ala Ala Leu Phe Pro Pro Glu Gly Ile
            115                 120                 125
Ser Ile Trp Asn Pro Arg Leu Leu Trp Gln Pro Ile Pro Val His Thr
            130                 135                 140
Val Ser Leu Ser Glu Asp Arg Leu Leu Tyr Leu Pro Phe Arg Asp Cys
145                 150                 155                 160
Pro Arg Phe Glu Glu Leu Lys Ser Glu Thr Leu Glu Ser Glu Glu Phe
                165                 170                 175
Leu Lys Arg Leu His Pro Tyr Lys Ser Phe Leu Asp Thr Leu Ser Ser
            180                 185                 190
Leu Ser Gly Phe Asp Asp Gln Asp Leu Phe Gly Ile Trp Ser Lys Val
            195                 200                 205
Tyr Asp Pro Leu Phe Cys Glu Ser Val His Asn Phe Thr Leu Pro Ser
            210                 215                 220
Trp Ala Thr Glu Asp Ala Met Ile Lys Leu Lys Glu Leu Ser Glu Leu
225                 230                 235                 240
Ser Leu Leu Ser Leu Tyr Gly Ile His Lys Gln Lys Glu Lys Ser Arg
                245                 250                 255
Leu Gln Gly Gly Val Leu Val Asn Glu Ile Leu Lys Asn Met Lys Leu
            260                 265                 270
Ala Thr Gln Pro Gln Lys Tyr Lys Lys Leu Val Met Tyr Ser Ala His
            275                 280                 285
Asp Thr Thr Val Ser Gly Leu Gln Met Ala Leu Asp Val Tyr Asn Gly
            290                 295                 300
Val Leu Pro Pro Tyr Ala Ser Cys His Met Met Glu Leu Tyr His Asp
305                 310                 315                 320
Lys Gly Gly His Phe Val Glu Met Tyr Tyr Arg Asn Glu Thr Gln Asn
                325                 330                 335
Glu Pro Tyr Pro Leu Thr Leu Pro Gly Cys Thr His Ser Cys Pro Leu
            340                 345                 350
Glu Lys Phe Ala Glu Leu Leu Asp Pro Val Ile Ser Gln Asp Trp Ala
            355                 360                 365
Thr Glu Cys Met Ala Thr Ser Ser His Gln Gly Arg Asn
            370                 375                 380

<210> SEQ ID NO 3
<211> LENGTH: 381
<212> TYPE: PRT
<213> ORGANISM: Rattus norvegicus

<400> SEQUENCE: 3

Met Arg Ala Val Pro Leu His Leu Val Gly Thr Ala Ser Leu Thr Leu
1               5                   10                  15
Gly Phe Leu Leu Leu Leu Ser Leu Arg Leu Asp Pro Gly Gln Ala Lys
                20                  25                  30
Glu Leu Lys Phe Val Thr Leu Val Phe Arg His Gly Asp Arg Gly Pro
            35                  40                  45
Ile Glu Thr Phe Pro Asn Asp Pro Ile Lys Glu Ser Ser Trp Pro Gln
        50                  55                  60
Gly Phe Gly Gln Leu Thr Lys Trp Gly Met Gly Gln His Tyr Glu Leu
65              70                  75                  80
```

-continued

```
Gly Ser Tyr Ile Arg Arg Tyr Gly Arg Phe Leu Asn Asn Ser Tyr
            85                  90                  95

Lys His Asp Gln Val Tyr Ile Arg Ser Thr Asp Val Asp Arg Thr Leu
            100                 105                 110

Met Ser Ala Met Thr Asn Leu Ala Ala Leu Phe Pro Pro Glu Gly Ile
            115                 120                 125

Ser Ile Trp Asn Pro Arg Leu Leu Trp Gln Pro Ile Pro Val His Thr
    130                 135                 140

Val Ser Leu Ser Glu Asp Arg Leu Leu Tyr Leu Pro Phe Arg Asp Cys
145                 150                 155                 160

Pro Arg Phe Gln Glu Leu Lys Ser Glu Thr Leu Lys Ser Glu Glu Phe
                165                 170                 175

Leu Lys Arg Leu Gln Pro Tyr Lys Ser Phe Ile Asp Thr Leu Pro Ser
                180                 185                 190

Leu Ser Gly Phe Glu Asp Gln Asp Leu Phe Glu Ile Trp Ser Arg Leu
                195                 200                 205

Tyr Asp Pro Leu Tyr Cys Glu Ser Val His Asn Phe Thr Phe Arg Thr
    210                 215                 220

Trp Ala Thr Glu Asp Ala Met Thr Lys Leu Lys Glu Leu Ser Glu Leu
225                 230                 235                 240

Ser Leu Leu Ser Leu Tyr Gly Ile His Lys Gln Lys Glu Lys Ser Arg
                245                 250                 255

Leu Gln Gly Gly Val Leu Val Asn Glu Ile Leu Lys Asn Met Lys Leu
                260                 265                 270

Ala Thr Gln Pro Gln Lys Ala Arg Lys Leu Ile Met Tyr Ser Ala Tyr
            275                 280                 285

Asp Thr Thr Val Ser Gly Leu Gln Met Ala Leu Glu Leu Tyr Asn Gly
    290                 295                 300

Leu Leu Pro Pro Tyr Ala Ser Cys His Ile Met Glu Leu Tyr Gln Asp
305                 310                 315                 320

Asn Gly Gly Thr Phe Val Glu Met Tyr Tyr Arg Asn Glu Thr Gln Asn
                325                 330                 335

Glu Pro Tyr Pro Leu Thr Leu Pro Gly Cys Thr His Ser Cys Pro Leu
                340                 345                 350

Glu Lys Phe Ala Glu Leu Leu Asp Pro Val Ile Pro Gln Asp Trp Ala
            355                 360                 365

Thr Glu Cys Met Gly Thr Ser Asn His Gln Ala Ser Leu
    370                 375                 380
```

METHODS AND COMPOSITIONS FOR TREATING PROSTATE CANCER USING DNA VACCINES

STATEMENT REGARDING FEDERALLY SPONSORED RESEARCH/DEVELOPMENT

This invention was made with government support under grant numbers CA085218, CA07516, CA068255, and DAMD 17-96-1-6322 awarded by the National Institutes of Health, and the U.S. Department of Defense, U.S. Army. The government has certain rights in the invention.

FIELD OF THE INVENTION

This invention relates to pharmaceutical compositions and methods using plasmid DNA vaccines for the treatment of prostate cancer. Specifically, this invention relates to the use of plasmids comprising a gene or polynucleotide sequence encoding prostatic acid phosphatase (PAP) for cancer the treatment of prostate.

BACKGROUND OF THE INVENTION

Prostate cancer continues to be a major health problem worldwide, with over 220,000 estimated new cases this year in the United States alone (Jemal et al., Cancer Statistics, 2003. (2003) CA A Canc. Jour. Clin., 53:5–26). It is the most common tumor diagnosed among men and the second leading cause of male cancer-related death in the United States (Jemal et al., Cancer Statistics, 2003. (2003) CA A Canc. Jour. Clin., 53:5–26). Despite advances in screening and early detection, approximately 30% of patients undergoing definitive prostatectomy or ablative radiation therapy will have recurrent disease at 10 years (Oefelein et al., Long-term results of radical retropubic prostatectomy in men with high grade carcinoma of the prostate (1997) J Urol, 158:1460–1465). At present, there is no accepted adjuvant treatment for patients undergoing radical prostatectomy or ablative radiation therapy that has been shown to prevent the progression to metastatic disease. In addition to new treatments for metastatic disease, new strategies are needed to eradicate microscopic disease to prevent the progression to clinically apparent metastasis.

In patients who have undergone definitive ablative therapy for prostate cancer, the presence of detectable serum levels of prostate-specific antigen (PSA) has provided a valuable indicator of microscopic metastatic disease. In a retrospective review of 1,997 men treated with radical prostatectomy, 15% were found to have evidence of a PSA-only recurrence over a median 5-year follow up, so-called stage D0 disease (Pound et al., Natural history of progression after PSA elevation following radical prostatectomy. (1999) JAMA 281:1591-7). Of these, 34% developed radiographically apparent metastatic disease, with a median time to development of metastatic disease of 8 years. In all patients with metastatic disease, the median time to death was 5 years Pound et al., Natural history of progression after PSA elevation following radical prostatectomy. (1999) JAMA 281:1591-7. These findings suggest that patients with stage D0 disease are at high risk for progressive disease, however with a long window of time to test adjuvant therapies. Similarly, many patients are found to have microscopic pelvic lymph node metastases at the time of radical prostatectomy, so-called stage D1 disease. At present, the best treatment for these patients is controversial, with some obtaining radical prostatectomy, other referred for radiation therapy with or without androgen deprivation therapy, and yet others are expectantly observed without specific treatment. In retrospective studies, 10-year disease-specific recurrence and mortality is on the order of 50 to 66% for patients with stage D1 disease (Sgrignoli et al., Prognostic factors in men with stage D1 prostate cancer: identification of patients less likely to have prolonged survival after radical prostatectomy. (1994) J Urol, 152:1077–81; Cadeddu et al., Stage D1 (T1-3, N1-3, M0) prostate cancer: a case-controlled comparison of conservative treatment versus radical prostatectomy. (1997) Urology, 50:251–5). This high-risk stage of minimal residual disease also provides an opportunity to test novel adjuvant therapies.

Immunological therapies, and vaccines in particular, are appealing as possible treatment options for prostate cancer for several reasons. Once a patient is diagnosed with presumably organ-confined prostate cancer, the prostate is usually removed by prostatectomy or destroyed in vivo with radiation. Hence, an immune response directed against the prostate that destroys any remaining prostate tissue following ablative therapy might be clinically beneficial to eradicate microscopic metastatic disease. The target of such immune-based therapy following ablative initial therapy would not need to be specific to malignant prostate tissue, but to any prostate tissue. In addition, such therapies may be relatively safe and inexpensive treatments compared with chemotherapies for a disease for which no standard adjuvant treatments exist (Kent et al., Immunity of prostate specific antigens in the clinical expression of prostatic carcinoma. (1976) In: Crispen R G, ed. Neoplasm immunity: mechanisms. Chicago, ITR, pp. 85–95; Guinan et al., Immunotherapy of prostate cancer: a review. (1984) Prostate, 5:221–230; McNeel et al., Tumor vaccines for the management of prostate cancer. (2000) Arch. Immunol. Ther. Exp., 48:85–93). Moreover, prostate cancer is a slow-growing disease, with typically over five years from the time of diagnosis of organ-confined disease to the development of clinically apparent metastatic disease. Such a slow-growing disease might be more amenable to vaccine-based treatments than a rapidly growing tumor, assuming that microscopic amounts of disease would be easier to treat than bulky or rapidly growing disease by vaccines. In fact, vaccines have already entered clinical trials for prostate cancer targeting a variety of prostate-specific proteins, with at least two dendritic cell-based vaccines suggesting clinical benefit in patients with low-volume metastatic disease (Murphy et al., Phase II prostate cancer vaccine trial: report of a study involving 37 patients with disease recurrence following primary treatment. (1999) Prostate, 39:54–59; Small et al., Immunotherapy of hormone-refractory prostate cancer with antigen-loaded dendritic cells. (2000) J. Clin. Oncol., 18:3894–3903).

PAP was first identified in the serum of patients with metastatic prostate cancer in 1938 (Gutman et al., An acid phosphatase in the serum of patients with metastasizing carcinoma of the prostate gland. (1938) J. Clin. Invest., 17:473–479). It was subsequently found to be expressed almost exclusively in normal and malignant prostate tissue, and used as a serum marker to follow the progression of the disease before more general use of the PSA serum protein marker (Siddall et al., An evaluation of the immunochemical measurement of prostatic acid phosphatase and prostatic specific antigen in carcinoma of the prostate. (1986) Eur. Urol., 12:123–130). The ubiquitous expression of PAP in prostate tissue makes it an appealing antigen as a potential universal target for immune-directed therapies of prostate cancer, unlike specific oncogenes that may or may not be expressed by a particular tumor. In addition, the discovery of the rodent homologue, rPAP, has provided an animal model for preclinical evaluation, as described below. Moreover, in human preclinical work, the present inventor has previously demonstrated that T cell responses of a Th1 phenotype specific for PAP can be detected in some patients with prostate cancer, suggesting that immune tolerance to this protein can be circumvented in vivo in at least a subset of patients, and consequently might be elicited and/or augmented by means of vaccines (McNeel et al., Naturally occurring prostate cancer antigen-specific T cell responses of a Th1 phenotype can be detected in patients with prostate cancer. (2001) Prostate, 47:222–229). Finally, vaccine trials targeting PAP have entered clinical testing and results of early phase studies suggest that immunity to this protein can be elicited or augmented in patients with prostate cancer by means of dendritic cell (DC)-based vaccines, in some cases with evidence of clinical benefit (Small et al., Immunotherapy of hormone-refractory prostate cancer with antigen-loaded dendritic cells. (2000) J. Clin. Oncol., 18:3894–3903; Burch et al., Priming tissue-specific cellular immunity in a phase I trial of autologous dendritic cells for prostate cancer. (2000) Clin. Cancer Res., 6:2175–2182; Fong et al., Dendritic Cell-Based Xenoantigen Vaccination for Prostate Cancer Immunotherapy. (2001) J Immunol, 167:7150–7156). A multi-site randomized, placebo-controlled phase III trial sponsored by Dendreon Corporation targeting PAP by means of a dendritic cell vaccine in patients with androgen-independent prostate cancer is currently underway based on these findings.

The use of plasmid DNA alone as a means of in vivo gene delivery by direct injection into muscle tissue was first described by Wolff et al. (Wolff et al., Direct gene transfer into mouse muscle in vivo. (1990) Science, 247:1465–1468). It was subsequently found that intramuscular or intradermal administration of plasmids expressing foreign genes elicited immune responses (Tang, et al., Genetic immunization is a simple method for eliciting an immune response. (1992) Nature, 356:152–154; Wang et al., Gene inoculation generates immune responses against human immunodeficiency virus type 1. (1993) Proc Natl. Acad. Sci. USA, 90:4156–4160; Raz et al., Intradermal gene immunization: the possible role of DNA uptake in the induction of cellular immunity to viruses. (1994) Proc Natl. Acad. Sci. USA, 91:9519–9523). This has quickly led to numerous investigations into the use of plasmid DNA as a means of vaccine antigen delivery, both in animal and human models. DNA vaccines, like peptide-based vaccines, are advantageous in being relatively easy and inexpensive to manufacture, and are not individualized for patients as are dendritic cell-based vaccines. Unlike recombinant protein vaccines, in which the antigen is taken up by antigen presenting cells and expressed predominantly in the context of MHC class II, animal studies have demonstrated that DNA in nucleic acid vaccines is taken up and expressed by antigen-presenting cells directly, leading to antigen presentation through naturally processed MHC class I and II epitopes (Iwasaki, et al. The dominant role of bone marrow-derived cells in CTL induction following plasmid DNA immunization at different sites. (1997) J Immunol, 159: 11–14). This method of immunization is consequently similar to the use of viral immunization vectors, however without the additional foreign antigens introduced with a viral vector and therefore with less risk of an overwhelming immune response to the vector itself (Irvine et al. The next wave of recombinant and synthetic anticancer vaccines. (1995) Seminars in Canc. Biol. 6:337–347). This direct expression by host cells, including MHC class I expressing bystander cells, has been demonstrated to lead to vigorous CD8+ CTL responses specific for the targeted antigen (Iwasaki et al., The dominant role of bone marrow-derived cells in CTL induction following plasmid DNA immunization at different sites. (1997) J. Immunol. 159:11–14; Chen et al., Induction of CD8+ T cell responses to dominant and subdominant epitopes and protective immunity to Sendai virus infection by DNA vaccination. (1998) J. Immunol., 160:2425–2432; Thomson et al., Delivery of multiple CD8 cytotoxic T cell epitopes by DNA vaccination. (1998) J. Immunol., 160:1717–1723; Cho et al., Immunostimulatory DNA-based vaccines induce cytotoxic lymphocyte activity by a T-helper cell-independent mechanism. (2000) Nat. Biotechnol. 18:509–514). In addition, plasmid DNA used for immunization may potentially stay present within cells at the site of immunization, providing a constant source of antigenic stimulation, rather than protein or peptide vaccines that are rapidly cleared by the reticuloendothelial system (Wolff et al., Direct gene transfer into mouse muscle in vivo. (1990) Science, 247:1465–1468; Tighe et al., Gene vaccination: plasmid DNA is more than just a blueprint. (1998) Immunol. Today, 19:89–97). It has been suggested that persistent antigen expression may lead to long-lived immunity (Raz et al., Intradermal gene immunization: the possible role of DNA uptake in the induction of cellular immunity to viruses. (1994) Proc. Natl. Acad. Sci. USA, 91:9519–9523). Given that a CTL response to PAP would be predicted based on the prior animal studies to be the most effective immune response in eliciting tissue destructive prostatitis, a DNA-based immunization would be predicted to be an ideal method of immunization in an MHC-diverse human population.

Recently, clinical trials have suggested that plasmid DNA vaccines are safe and immunologically effective in humans. Boyer and colleagues reported that doses of 300 µg of plasmid DNA encoding HIV rev and env proteins administered intramuscularly were capable of eliciting antigen-specific, IFNγ-secreting T cell responses in HIV-seronegative patients (Boyer et al., Vaccination of seronegative volunteers with a human immunodeficiency virus type 1 env/rev DNA vaccine induces antigen-specific proliferation and lymphocyte production of beta-chemokines. (2000) J. Infect. Dis. 181:476–83). In addition, results of a clinical trial targeting prostate-specific membrane antigen (PSMA) in patients with prostate cancer by means of plasmid DNA and adenovirus have been reported (Mincheff et al., Naked DNA and Adenoviral Immunizations for Immunotherapy of Prostate Cancer: A Phase I/II Clinical Trial. (2000) Eur. Urol., 38:208–217). In this study, 26 patients were immunized either in a prime/boost strategy with an adenoviral vector expressing PSMA followed by immunization with plasmid DNA expressing PSMA, or with plasmid DNA alone. The authors report no significant toxicity with doses of 100–800 µg of plasmid DNA administered intradermally, and suggest that patients receiving plasmid DNA expressing PSMA and CD86 with soluble GM-CSF as an adjuvant were all successfully immunized (Mincheff et al., Naked DNA and Adenoviral Immunizations for Immunotherapy of Prostate Cancer: A Phase I/II Clinical Trial. (2000) Eur. Urol., 38:208–217).

Previous work in rodent models has shown that a cytotoxic cellular immune response (CTL) specific for PAP elicits prostate tissue inflammation, and the destruction of normal rat prostate tissue (Fong et al., 1997, J. Immunol. 159:3113–3117; McNeel and Disis, 1999, Proc. Amer. Assn Canc. Res. 40:256). In addition, McNeel et al. demonstrated that T cell responses of a Th1 phenotype specific for PAP could be detected in some patients with prostate cancer, suggesting that immune tolerance to this autoantigen can be circumvented in vivo in at least some patients, and that host immune reaction to this protein might be augmented by means of vaccines (McNeel et al., 2001, Prostate 47:222–229).

Dendritic cell (DC)-based and protein-based vaccines have been tested for the treatment of prostate cancer. DC-based vaccine trials targeting PAP have entered clinical testing and results of early phase studies suggest that immunity to this protein can be elicited or augmented in patients with prostate cancer (Burch et al., 2000, P, Clin. Cancer Res. 6:2175–2182; Fong et al., 2001, J. Immunol, 167:7150–7156). Dendritic cell-based vaccines, however, must be individualized for each patient, and as a consequence are costly and cumbersome in large-scale application. Protein based vaccines, on the other hand, are taken up by antigen presenting cells and expressed predominantly in the context of MHC class II, thus often are difficult to be delivered effectively and may not induce robust immune response to the antigen. In addition, protein or peptide vaccines are rapidly cleared by the reticuloendothelial system (Wolff et al., 1990, Science 247:1465–8; Tighe et al., 1998, Immunol. Today 19:89–97.)

There is, therefore, a need for an improved method that overcome the short falls of the above existing methods.

SUMMARY OF THE INVENTION

The invention provides a method for inducing an immune reaction to prostatic acid phosphatase (PAP) in a mammal in need thereof, the method comprising administering to the mammal an effective amount of a recombinant DNA construct comprising a polynucleotide sequence encoding PAP operatively linked to a transcriptional regulatory element, whereby the mammal develops an immune reaction against PAP. In a preferred embodiment, the mammal, preferably a human, is a prostate cancer patient.

Preferably, the polynucleotide sequence encoding PAP is a human PAP gene. In another embodiment, the polynucleotide sequence encoding PAP is a rodent PAP gene.

According to the invention, the recombinant DNA construct is administered to the mammal intramuscularly or intravascularly, including intravenously and intraarterially.

The method according to the present invention induces cytotoxic immune reaction against cells expressing PAP. Preferably, both humoral and cellular immune reactions against PAP are induced. The method according to the invention preferably induces destructive prostatitis in the mammal. Most preferably, cancer cells expression PAP are selectively killed by the method of the present invention.

In a preferred embodiment, the method of the present invention employs a "prime-boost" strategy, which comprises administering to the mammal an effective amount of a first recombinant DNA construct comprising a first polynucleotide sequence encoding a first PAP polypeptide operatively linked to a transcriptional regulatory element; followed by administering to the mammal an effective amount of a second recombinant DNA construct comprising a second polynucleotide sequence encoding a second PAP polypeptide operatively linked to a transcriptional regulatory element; wherein the first polynucleotide sequence and the second polynucleotide molecule originate from two different animal species, whereby an immune reaction against PAP is induced in the mammal. In one embodiment, the first polynucleotide sequence originates from an animal species other than the mammal, and the second polynucleotide sequence originates from the same animal species as the mammal. Preferably, the mammal is a human, and the first polynucleotide sequence encoding PAP originates from a rodent. In another embodiment, the second polynucleotide sequence originates from the same animal species as the mammal, and the first polynucleotide sequence encodes a PAP polypeptide that shares at least 85%, preferably at least 88%, still more preferably at least 90%, more preferably at least 95%, and most preferably at least 98% homology to the first PAP polypeptide.

According to another aspect of the present invention, a DNA vaccine is contemplated which comprises a plasmid vector comprising a polynucleotide sequence encoding prostatic acid phosphatase operably linked to a transcription regulatory element, wherein upon administration to a mammal a cytotoxic immune reaction against cells expressing PAP is induced in the mammal. The vaccine of the present invention preferably is suitable for intradermal, intramuscular or intraarterial administration to a human. According to a preferred embodiment, the plasmid vector comprises a backbone of pNGVL3, a polynucleotide sequence encoding PAP operably inserted therein, and one or a plurality of an immuno-stimulatory sequence (ISS) motif.

Preferably, the DNA vaccine according to the invention comprises a plasmid vector that comprises a polynucleotide sequence encoding PAP operatively linked to a CMV promoter; a CMV intron A operatively linked to the polynucleotide sequence encoding PAP for enhancing expression of the polynucleotide sequence; and at least one copy of an immuno-stimulatory fragment comprising 5'-GTCGTT-3'. In one embodiment, the plasmid construct does not express in eukaryotic cells any gene other than the polynucleotide sequence encoding PAP. The plasmid vector pTVG4 is particularly preferred.

Also disclosed are pharmaceutical compositions comprising the DNA vaccine of the invention, and a pharmaceutically acceptable carrier. Preferably, the pharmaceutical composition of the invention comprises the DNA vaccine and further a suitable amount of immuno-stimulant such as GM-CSF, optionally with a pharmaceutically acceptable carrier.

BRIEF DESCRIPTION OF THE DRAWINGS

FIG. 1 shows male Lewis rats immunized with human PAP protein develop a proliferative T cell response to human PAP and a cross-reactive antibody response.

FIG. 9A shows Lewis rats immunized with vaccinia virus expressing human PAP develop evidence of autoimmune prostatitis. Lewis rats were immunized subcutaneously on day 1 with $2 \times 10^7$ pfu of vaccinia virus expressing PAP and then boosted on day 15 with either recombinant vaccinia virus (panel A), or 25 µg purified PAP administered s.c. in CFA adjuvant (panel B). Splenocytes from immunized animals were cultured for 96 hours in the presence of 2.0 µg/ml human PAP, 2.5 µg/ml PHA, or no antigen. Culture supernatants were then assayed for IFNγ concentration by quantitative ELISA. IFNγ concentration is shown for a control experimental animal that did not develop prostatitis (panel A), and one which did (panel B). The animals were sacrificed 8 weeks later on day 57. FIG. 9B shows a prostate biopsy stained with hematoxylin and eosin.

FIG. 13 shows that administration of pTVG-HP elicits PAP-specific IgG antibodies, predominantly of IgG2b subtype. Sera was obtained from animals immunized twice at 2-week intervals with PAP protein in Freund's adjuvant (n=3), or once with 750 µg of pTVG-HP administered intraarterially (n=3). Sera were screened for PAP-specific IgG using an indirect ELISA, and IgG subtypes were determined using an IgG1-specific secondary antibody (panel A), or an IgG2b-specific secondary antibody (panel B). Results shown are the mean and standard error of three experimental animals in each group.

FIG. 15 shows Lewis rats immunized with plasmid DNA encoding human PAP develop evidence of autoimmune prostatitis. Lewis rats were immunized intradermally on days 1 and 15 with 50 μg of plasmid DNA encoding either no antigen (A) or human PAP (B) along with murine granulocyte-macrophage colony-stimulating factor (GM-CSF) as a vaccine adjuvant. Two weeks after the 2nd immunization animals were sacrificed and prostate biopsies obtained. The figure shows biopsies stained with hematoxylin and eosin.

FIG. 19 shows an alignment of the amino acid sequences of the PAP protein (SEQ ID NO:1); mouse PAP protein (SEQ ID NO:2), and rat PAP protein (SEQ ID NO:3).

DETAILED DESCRIPTION OF PREFERRED EMBODIMENTS

Figure 1A:
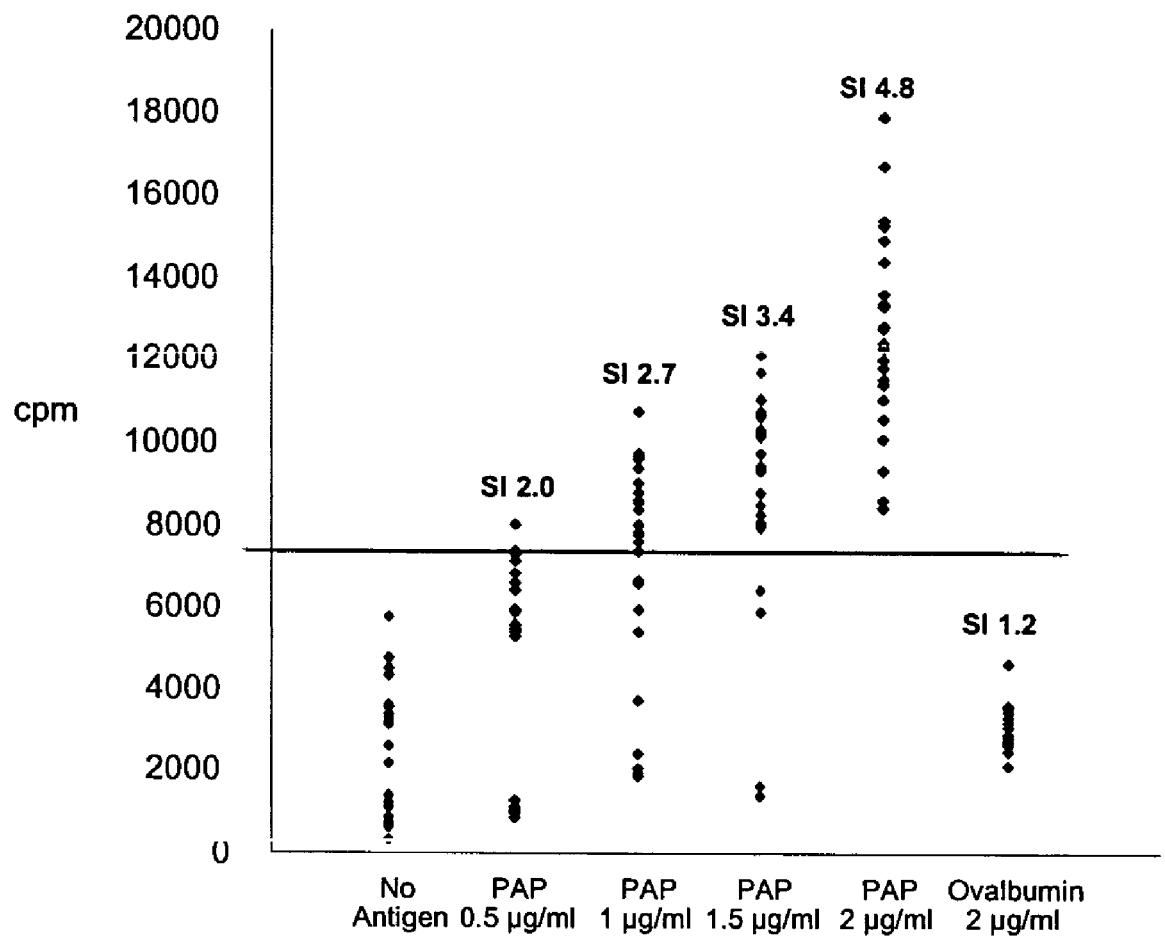
In FIG. 1A, human PAP and ovalbumin, as negative control, were used as test antigens for primed T cell responses in a 3H-thymidine incorporation assay. The numbers indicate stimulation indices compared with the no-antigen control wells.

This invention provides pharmaceutical compositions and methods using plasmid DNA vaccines for the treatment of prostate cancer. Specifically, this invention provides recombinant plasmid vectors comprising genes or polynucleotide molecules encoding prostatic acid phosphatase (PAP) for treating prostate cancer.

The vaccines of the present invention, when directly introduced into a vertebrate in vivo, including mammals such as humans, induce the expression of encoded proteins within the animal, and cause the animal's immune system to become reactive against the proteins. The vaccines may be any polynucleotides that are capable of generating immune responses to an encoded protein. The vaccines are referred to herein as polynucleotide vaccines. Preferably, the polynucleotide vaccines of the present invention are DNA vaccines, especially plasmid DNA vaccines.

The instant invention also provides a method for using a polynucleotide which, upon introduction into a vertebrate, induces the expression, in vivo, of the polynucleotide thereby producing the encoded protein, and causes the vertebrate to become immune reactive against the protein so produced.

DNA vaccines, like peptide-based vaccines, are advantageous in being relatively easy and inexpensive to manufacture, and are not individualized for patients, as are dendritic cell-based vaccines. Unlike recombinant protein vaccines, in which the antigen is taken up by antigen presenting cells and expressed predominantly in the context of MHC class II, DNA in nucleic acid vaccines is taken up and expressed by antigen-presenting cells directly, leading to antigen presentation through both naturally processed MHC class I and II epitopes (Iwasak et al., 1997, J. Immunol. 159:11–4).

Given their potential ability to elicit antigen-specific cytotoxic T-cell (CTL) immunity in an MHC class I diverse population, DNA-based vaccines for various diseases have recently entered human clinical trials (Mincheff et al., 2000, Eur. Urol., 38:208–217). This method of immunization is similar to the use of viral immunization vectors, but without the additional foreign antigens introduced with a viral vector and therefore with less risk of an overwhelming immune response to the vector itself (Irvine and Restifo, 1995, Seminars in Canc. Biol. 6:337–347). Direct expression by host cells, including MHC class I-expressing bystander cells, has been demonstrated to lead to vigorous CD8+ CTL responses specific for the targeted antigen (Iwasak et al., 1997, J. Immunol. 159:11–4; Chen et al., 1998, J. Immunol. 160:2425–2432; Thomson et al., 1998, J. Immunol. 160:1717–1723; Cho et al., 2000, Nat. Biotechnol, 18:509–14). In addition, plasmid DNA used for immunization may remain within cells at the site of immunization, providing a constant source of antigenic stimulation, rather than protein or peptide vaccines that are rapidly cleared by the reticuloendothelial system (Wolff et al., 1990, Science 247:1465–8; Tighe et al., 1998, Immunol. Today 19:89–97). Persistent antigen expression may lead to long-lived immunity (Raz et al., 1994, Proc. Natl. Acad. Sci. USA 91:9519–23).

The present invention provides DNA-based vaccines that express a protein antigen, prostatic acid phosphatase, and methods for treating prostate cancers in an animal using the vaccines. In addition to the reasons explained above, plasmid vaccines are advantageous over viral vaccines. For example, viral vaccines are not amenable to repeated immunizations. With viral vectors, one is trying to elicit an immune response against a "self" protein encoded by a foreign virus. The immune system preferentially recognizes the foreign proteins, sometimes hundreds of proteins, encoded by the virus. The present inventor has found in rats that repeated immunizations with a vaccinia virus encoding hPAP elicits a strong vaccinia response but no hPAP-specific response. That same finding has now been shown in humans, in a trial in which repeated immunization with the vaccinia virus encoding human PSA elicited weak PSA-specific immunity, but potent vaccinia immunity (Sanda et al., 1999, Urology 53:260). The direction in the field of viral-based vaccines is to "prime" with a virus encoding the antigen, and then "boost" with a different virus (like adenovirus or fowl pox) encoding the same antigen. The advantage of plasmid DNA vaccines is that they encode a defined, often small, number of proteins. And therefore one can repetitively immunize the animal patient. Furthermore, a virus may kill cells, incorporate into the genome, or potentially induce other unwanted immune responses. All these are disadvantages that are likely avoided by DNA plasmid vaccines.

It is readily recognizable that a PAP gene of any origin, or any of its derivative, equivalents, variants, mutants etc., is suitable for the instant invention, as long as the protein encoded by the genes, or derivatives, equivalents, variants, or mutants there of are able to induce an immune reaction in the host animal substantially similar to that induced by an autoantigenic or xenoantigenic PAP protein in the animal.

PAP genes are known and have been cloned from human, mouse and rat. FIG. 19 shows an alignment of the amino acid sequences of the three PAP proteins. As will be readily recognized by one of ordinary skills in the art, any DNA sequence that encode one of these three amino acid sequences are suitable for the present invention, and any other PAP genes from other animals, as they become identified, characterized and cloned are also suitable for the present invention. Dogs and non-human primates are known to have PAP genes.

As is well-known to those skilled in the art, polypeptides having substantial sequence similarities cause identical or very similar immune reaction in a host animal. As discussed below, this phenomenon is the basis for using a xenoantigen for inducing autoreactive reaction to an otherwise tolerated autoantigen. Accordingly, any DNA sequences encoding a derivative, equivalent, variant, fragment, or mutant of any of the known or to-be-identified PAP proteins is also suitable for the present invention. The polypeptide encoded by these DNA sequences may be functional PAP enzyme, but do not necessarily have to be enzymatically functional, as long as the polypeptide encoded by these are structurally similar to the autologous PAP, and are sufficiently immunogenic.

It is readily apparent to those ordinarily skilled in the art that variations or derivatives of the nucleotide sequence encoding the protein antigen can be produced which alter the amino acid sequence of the encoded protein. The altered expressed protein may have an altered amino acid sequence, for example by conservative substitution, yet still elicits immune responses which react with the protein antigen, and are considered functional equivalents. According to a preferred embodiment, the derivative, equivalents, variants, fragments or mutants of a PAP enzyme are polypeptides that are at least 85% homologous to the human PAP sequence of SEQ ID NO:1. More preferably, the homology is at least 88%, preferably at least 90%, still more preferably at least 95%, and still more preferably at least 95%. Homology between amino acid sequences or between nucleotide sequences may be determined either manually by one skilled in the art, or by using computer-based sequence comparison and identification tools that employ algorithms such as BLAST (Basic Local Alignment Search Tool; Altschul et al. (1993) J. Mol. Biol. 215:403–410).

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following tables.

TABLE A

Conservative Substitutions I

| SIDE CHAIN CHARACTERISTIC | AMINO ACID |
|---|---|
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, Biochemistry, Second Edition; Worth Publishers, Inc. New York (1975), pp. 71–77, as set out in the following Table B.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |

TABLE C-continued

Conservative Substitutions III

| Original Residue | Exemplary Substitution |
| --- | --- |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

In addition, fragments of the full-length genes which encode portions of the full-length protein may also be constructed. These fragments may encode a protein or peptide which elicits humoral or cytotoxic reaction, or both, against the protein antigen, and are considered functional equivalents.

The PAP gene is preferably ligated into an expression vector which has been specifically optimized for polynucleotide vaccinations. Elements include a transcriptional promoter, immunogenic epitopes, and additional cistrons encoding immunoenhancing or immunomodulatory genes, with their own promoters, transcriptional terminator, bacterial origin of replication and antibiotic resistance gene, as well known to those skilled in the art. Optionally, the vector may contain internal ribosome entry sites (IRES) for the expression of polycistronic mRNA.

In one embodiment of this invention, a gene encoding a PAP protein is directly linked to a transcriptional promoter. The use of tissue-specific promoters or enhancers, for example the muscle creatine kinase (MCK) enhancer element may be desirable to limit expression of the polynucleotide to a particular tissue type. For example, myocytes are terminally differentiated cells which do not divide. Integration of foreign DNA into chromosomes appears to require both cell division and protein synthesis. Thus, limiting protein expression to non-dividing cells such as myocytes may be preferable. In addition, a PSA promoter may be used to limit expression of the protein to prostate tissue. In one embodiment, tissue- or cell-specific promoters may be used to target the expression of the protein to antigen-presenting cells. For example, an alpha-fetoprotein (AFP) promoter (see e.g. Peyton et al. 2000, Proc. Natl. Acad. Sci., USA. 97:10890–10894) may be used to limit expression to liver tissues. However, use of the CMV promoter is adequate for achieving expression in many tissues into which the plasmid DNA vaccine is introduced.

Suitable vectors suitable vectors include any plasmid DNA construct encoding a PAP antigen or a functional equivalent or derivative thereof, operatively linked to a eukaryotic promoter. Examples of such vectors include the pCMV series of expression vectors, commercially available from Stratagene (La Jolla, Calif.); or the pCDNA or pREP series of expression vectors by Invitrogen Corporation (Carlsbad, Calif.).

There are many embodiments of the instant invention which those skilled in the art can appreciate from the specification. Thus, different transcriptional promoters, terminators, and other transcriptional regulatory elements may be used successfully. Examples of other eukaryotic transcription promoters include the Rous sarcoma virus (RSV) promoter, the simian virus 40 (SV40) promoter, the human elongation factor-1α (EF-1α) promoter, and the human ubiquitin C (UbC) promoter.

The vectors of the present invention may be delivered intradermally, intramuscularly, intravascularly (including intraarterially). In preferred embodiments, delivery may be a combination of two or more of the various delivery methods.

In a particularly preferred embodiment, the animal in need of treatment may be first primed with a vector of the present invention comprising a xenoantigen, followed by a boosting with another vector comprising the same or a different xenoantigen, or an autoantigen, to achieve a robust and long lasting immune response against prostate cells. Both priming and boosting may be by any of the intradermal, intramuscular and intravascular delivery methods.

"Naked" plasmid DNA expressing a transgene could be directly injected intradermally or intramuscularly, taken up, and expressed (see e.g. Wolff et al., 1990, Science 247: 1465–8). The efficiency of this approach may be low, with only a small percentage of myocytes being directly transformed in vivo, and within only a limited area of muscle tissue targeted by this directed delivery. Various alternative approaches yielding a higher efficiency gene delivery method are known (see e.g. Acsadi et al., 1991, New Biol. 3:71–81). Subsequent work on strategies that increase uptake of plasmid DNA by muscle tissue focused on various carrier solutions and molecules (Wolff et. al., 1991, Biotechniques 11:474–85; Budker et al., 1996, Nat. Biotechnol. 14:760–4), the use of myotoxic agents to enhance DNA uptake (Davis et al., 1993, Hum. Gene Ther. 4:151–9; Danko et al., 1994, Gene Ther. 1:114–21), and the use of various transcriptional promoters and plasmid DNA backbones (Manthorpe et al., 1993, Hum. Gene Ther. 4:419–31).

In a preferred embodiment, plasmid vectors of the present invention may be delivered to the patient in need thereof intravascularly. Plasmid DNA delivered intravascularly resulted in 100-fold higher uptake in downstream tissues in rodent studies (Budker et al., 1996, Gene Ther. 3:593–8). Intravascular delivery may be intravenal, e.g. by direct injection of plasmid DNA into the portal vein of rodents with uptake and expression demonstrated in hepatocytes (Budker et al., 1996, Gene Ther. 3:593–8; Zhang et al., 1997, Hum. Gene Ther. 8:1763–72). Intravascular delivery may also be performed more directly by intraarterial delivery. For example, initial studies in rodents demonstrated that high levels of gene expression in hind limb muscle could be obtained by rapid injection of plasmid DNA into the femoral artery (Budker et al., 1998, Gene Ther. 5:272–276). This approach is efficient and safe in non-human primates as well, with an average of 7% of downstream myofibers expressing a β-galactosidase reporter construct two weeks after intraarterial DNA administration (Zhang et al., 2001, Hum. Gene Ther. 12:427–438). Parallel studies in T cell immuno-suppressed rats showed that gene expression was stable for at least 10 weeks (Zhang et al., 2001, Hum. Gene Ther. 12:427–438).

Accordingly, delivery of plasmid DNA vaccines of the present invention is preferably by direct intraarterial administration. This method delivers more effectively to MHC class I expressing cells. Administrations of plasmid DNA vaccines intravascularly result in increased antigen expression and subsequently lead to enhanced immune responses, and increased antigen expression in MHC class I expressing cells by means of intraarterial delivery of DNA plasmid will lead to a more robust immune response with PAP-specific CTL. An intraarterial method of DNA delivery are at least as effective or more effective than traditional intradermal administration of DNA in eliciting PAP-specific immunity and prostate tissue inflammation.

In another embodiment, intravenous delivery may also be used, employing methods well known to those skilled in the art (See e.g. Budker et al., 1998, Gene Ther. 5:272–276; Budker et al., 1996, Gene Ther. 3:593–598). This delivery method may lead to a high level of antigen expression in hepatocytes. Expression of the antigen in liver, a tissue more rich with antigen-presenting cells, may lead to a more pronounced Th1/CTL response than expression in muscle tissue.

The DNA vaccines of the present invention are preferably used in a prime-boost strategy to induce robust and long-lasting immune response to PAP. Priming and boosting vaccination protocols based on repeated injections of the same antigenic construct are well known and result in strong CTL responses. In general, the first dose may not produce protective immunity, but only "primes" the immune system. A protective immune response develops after the second or third dose.

In one embodiment, the DNA vaccines of the present invention may be used in a conventional prime-boost strategy, in which the same antigen is administered to the animal in multiple doses. In a preferred embodiment, the DNA vaccine is used in one or more inoculations. These boosts are performed according to conventional techniques, and can be further optimized empirically in terms of schedule of administration, route of administration, choice of adjuvant, dose, and potential sequence when administered with another vaccine, therapy or homologous vaccine (such as a plasmid DNA encoding a rodent PAP gene).

The DNA vaccines of the present invention are preferably used in a prime-boost strategy using an alternative administration of xenoantigen- and autoantigen-encoding vectors. Specifically, according to the present invention, the animal is first treated, or "primed," with a DNA vaccine encoding an antigen of foreign origin (a "xenoantigen"). Subsequently, the animal is then treated with another DNA vaccine encoding an antigen which is corresponding to the xenoantigen, but is of self origin ("autoantigen"). This way, the immune reaction to the antigen is boosted. The boosting step may be repeated one or more times.

A xenoantigen, as compared to a self-antigen or an autoantigen, is an antigen originated in or derived from a species different from the species that generates an immune reaction against the antigen. Xenoantigens usually are highly homologous molecules to a corresponding autoantigen. Xenoantigens have been shown to be able to elicit auto-reactive immunity. For example, molecular mimicry by highly homologous viral antigens has been one theory to explain the occurrence of several autoimmune diseases (von Herrat and Oldstone, 1996, Curr. Opin. Immunol. 8:878–885; Oldstone, 1998, Faseb J. 12:1255–1265). That is, the induction of immune responses following infection by viral antigens that closely resemble normal autologous proteins may then lead to an autoimmune reaction to the autologous protein.

The use of highly homologous foreign antigens or xenoantigens as vaccine antigens to elicit autoreactive immunity has been explored in animal models. For example, xenoantigens derived from zona pellucida of foreign species can elicit autoreactive T cell responses and disrupt ovarian function in a variety of animal species studied (Mahi-Brown et al., 1992, J. Reprod. Immunol. 21:29–46; Mahi-Brown, 1996, J. Reprod. Fertil. Suppl. 50:165–74).

The use of human PAP (hPAP) as a vaccine antigen to elicit immunity to rodent PAP (rPAP) in the Lewis rat is itself a further example of the concept of xenoantigen immunization. In fact, the use of a xenoantigen as a vaccine antigen has recently entered clinical testing in the context of a dendritic cell vaccine, and has suggested that autoreactive immune responses might be elicited in humans (Fong et al., 2001, supra). While not wishing to be bound by any theory on mechanism, it is believed that because T cells involved in autoimmune processes recognize peptide epitopes presented in the context of MHC molecules, the uptake and MHC presentation of a homologous foreign antigen presumably exposes T cell epitopes with enhanced MHC binding or unmasks cryptic epitopes of the native antigen not normally recognized.

While the prime-boost strategy is known to work with antigens of different origins, it is readily apparent to those ordinarily skilled in the art that variants, derivatives or equivalents, as discussed above, of the nucleotide sequence encoding a self-antigen can also be used to achieve the same results as xenoantigens.

The present invention will now be illustrated in more detail in the following examples. It is to be understood that these examples serve only to describe the specific embodiments of the present invention, but do not in any way limit the scope of the claims.

EXAMPLES

Example 1

Figure 1B:
In FIG. 1B, sera from an immunized rat were used to evaluate PAP-specific antibody responses in a Western blot experiment. Lane 1, protein standard; lane 2, human PAP (over-expressed from pQE-hPAP in E. coli); lane 3, rat PAP (over-expressed from pQE-rPAP in E. coli).

Rats Immunized with hPAP Protein Develop Cross-reactive Immunity to rPAP and Immunization with hPAP Protein Elicits Helper T Cells and Antibodies but Not Prostate Inflammation Lewis rats, when immunized with hPAP protein in Freund's adjuvant, developed a proliferative T cell and antibody response specific for hPAP (FIG. 1). Splenocytes from immunized rats were prepared by gradient centrifugation (Histopaque, Sigma). In FIG. 1A, human PAP (Research Diagnostics Inc., Flanders, N.J.) and ovalbumin, as a negative control protein, were used as test antigens for primed T cell responses in a 3H-thymidine incorporation assay. The numbers indicate stimulation indices compared with the no antigen control wells. In FIG. 1B, sera from an immunized rat were used to evaluate PAP-specific antibody responses in a Western blot experiment. Lane 1, protein standard; lane 2, human PAP (overexpressed from pQE-hPAP in E. coli); lane 3, rat PAP (overexpressed from pQE-rPAP in E. coli). The plasmids pQE-hPAP and pQE-rPAP were plasmid DNA constructs in which the cDNAs for human PAP or rat PAP, respectively, were cloned into the prokaryotic expression vector pQE-30 (Qiagen Inc., Valencia, Calif.) to drive expression of each of these gene products in E. coli.

A cross-reactive antibody response in these animals recognized the rat PAP protein (FIG. 1B); this response is not seen in control animals (data not shown). This immunization, however, does not lead to autoreactive prostate tissue inflammation (data not shown).

Example 2

Figure 2:
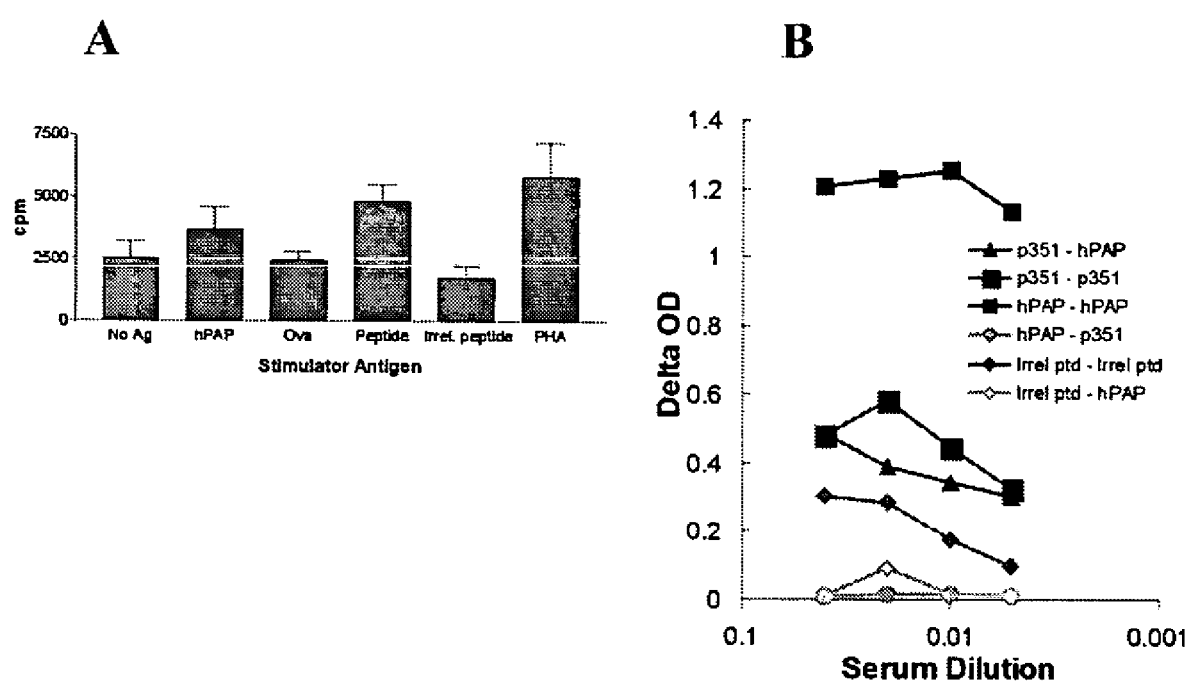
FIG. 2 shows that male Lewis rats immunized with peptides derived from HPAP develop PAP-specific immune responses. (A) Splenocytes from an animal immunized three times with p351 from hPAP were tested in a 3H-thymidine incorporation assay for antigen-specific T cell proliferation. Stimulator antigens included hPAP, the p351 peptide, ovalbumin and an irrelevant peptide as negative controls, and PHA as a positive control. Shown are the mean and standard deviation of 12-well replicates. (B). Sera from immunized animals were tested in an indirect ELISA for peptide-specific or hPAP protein-specific IgG responses. Animals immunized with p351 developed peptide-specific (p351-p351) and protein-specific (p351-hPAP) responses. Animals immunized with hPAP developed strong protein-specific (hPAP-hPAP) but not p351-specific (hPAP-351) responses. Animals immunized with control peptide developed peptide-specific responses (Irel ptd-Irel ptd), but not hPAP-specific responses (Irel ptd-hPAP).

Male Lewis Rats Immunized with Peptides Derived from hPAP Develop PAP-specific Immune Responses Male Lewis rats were immunized three times at 14-day intervals with 50 µg of one of ten distinct 15-mer peptides derived from the amino acid sequence of hPAP using Freund's adjuvant (McNeel et al. 2001, Cancer Res., 61:5161–5167). FIG. 2 demonstrates results from one such peptide, p351, compared with an irrelevant 15-mer peptide. Immunization with the p351 peptide elicited a peptide-specific and hPAP protein-specific T cell proliferative response (panel A). In addition, an antibody response specific for hPAP protein could be detected in p351-immunized rats (panel B). The absence of a peptide-specific antibody response in animals immunized with hPAP protein (panel B) suggests this may be a subdominant epitope of hPAP.

Example 3

Figure 3:
FIG. 3 shows that mRNAs encoding hPAP, rPAP and control antigen have been prepared. mRNAs encoding GFP (lane 3), hPAP (lane 4), and rPAP (lane 5) were prepared by in vitro transcription. Lane 1 demonstrates a negative control reaction (no DNA template), and lane 2 demonstrates a positive DNA template control.

DNA Vaccines Encoding Either Human or Rat PAP Elicit Potent Antigen-specific Cellular Immunity in Rodent and Human in vitro Models 1. Preparation of mRNA encoding hPAP, rPAP and control antigen.

mRNA encoding the green fluorescent protein (GFP), hPAP, or rPAP was prepared by in vitro transcription using the Ribomax transcription kit Promega (Madison, Wis.). In each case, in vitro transcription was performed using linearized plasmid DNA carrying the cDNA for the respective gene downstream of the T7 bacteriophage promoter. The sizes of the mRNA products were then confirmed on agarose gel (FIG. 3). These mRNA products are used for the experiments described below.

2. Construction of pTVG4

Figure 4:
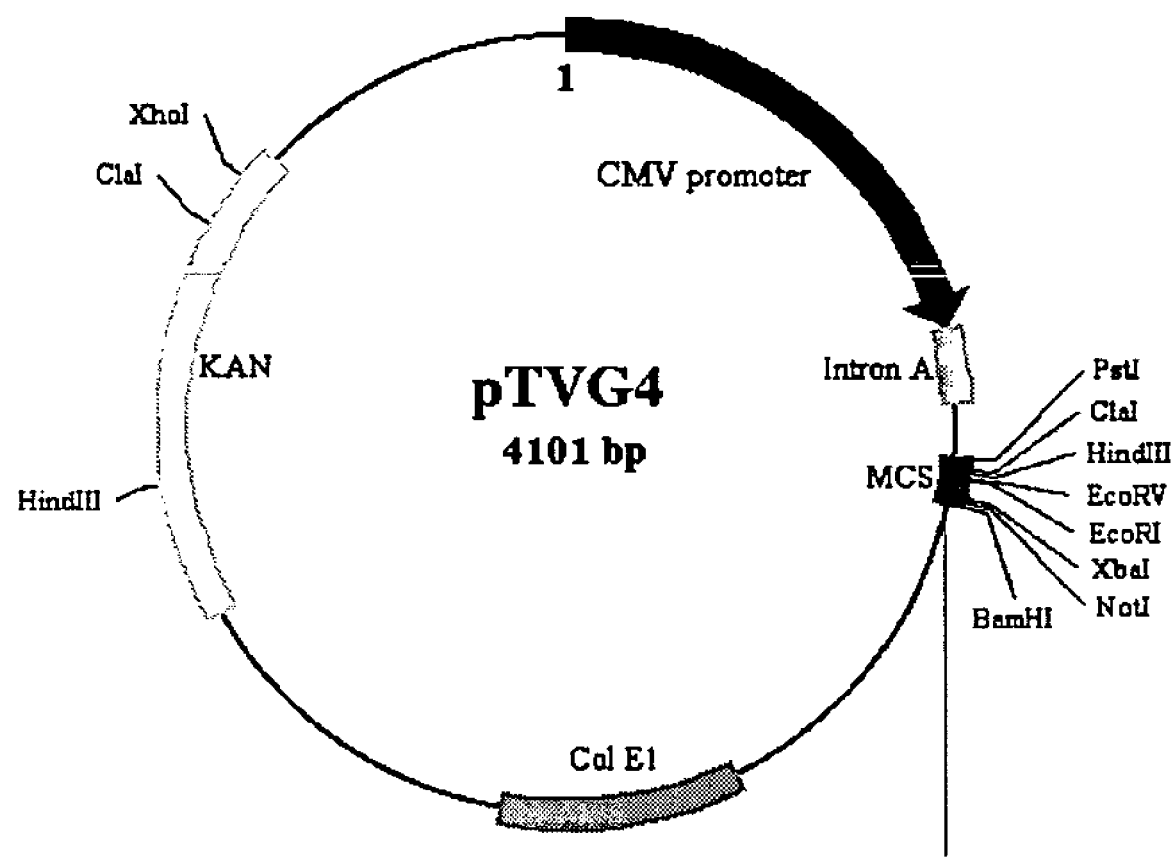
FIG. 4 depicts the plasmid map of pTVG4.

Plasmid DNA expression vectors have been developed for use in human vaccines. Shown in FIG. 4 is a plasmid map for the pTVG4 vector as constructed for rat immunization experiments and human trials. Into this construct has been inserted the coding sequence for the human PAP gene, to create the immunization vector pTVG-HP (see below).

The plasmid vector pNGVL3 was obtained from the National Gene Vector Laboratory at the University of Michigan (courtesy, Dr. Robert Gerard). This vector, similar to the pCDNA3.1 expression vector used above, drives transcription from the CMV promoter, but also includes the CMV intron A sequence to enhance protein expression (Lee et al., 1997, Mol. Cells 7:495–501). The vector also contains a multi-cloning site, and does not express a eukaryotic antibiotic resistance gene, such that the only protein expression expected in a eukaryotic system is the one driven from the CMV promoter, unlike the pCDNA vector. To this vector has been added 2 copies of a 36-bp immunostimulatory (ISS) fragment containing the 5'-GTCGTT-3' motif previously identified (Hartmann et al., 2000, J. Immunol. 164:1617–24), to create the vector pTVG4 (FIG. 4). The coding sequence for human PAP has been cloned into this vector, and expression of PAP has been confirmed by in vitro expression studies (not shown). This construct, named pTVG-HP, is used for the immunization studies.

3. Construction of pTVG-HP for human clinical trials

Figure 5:
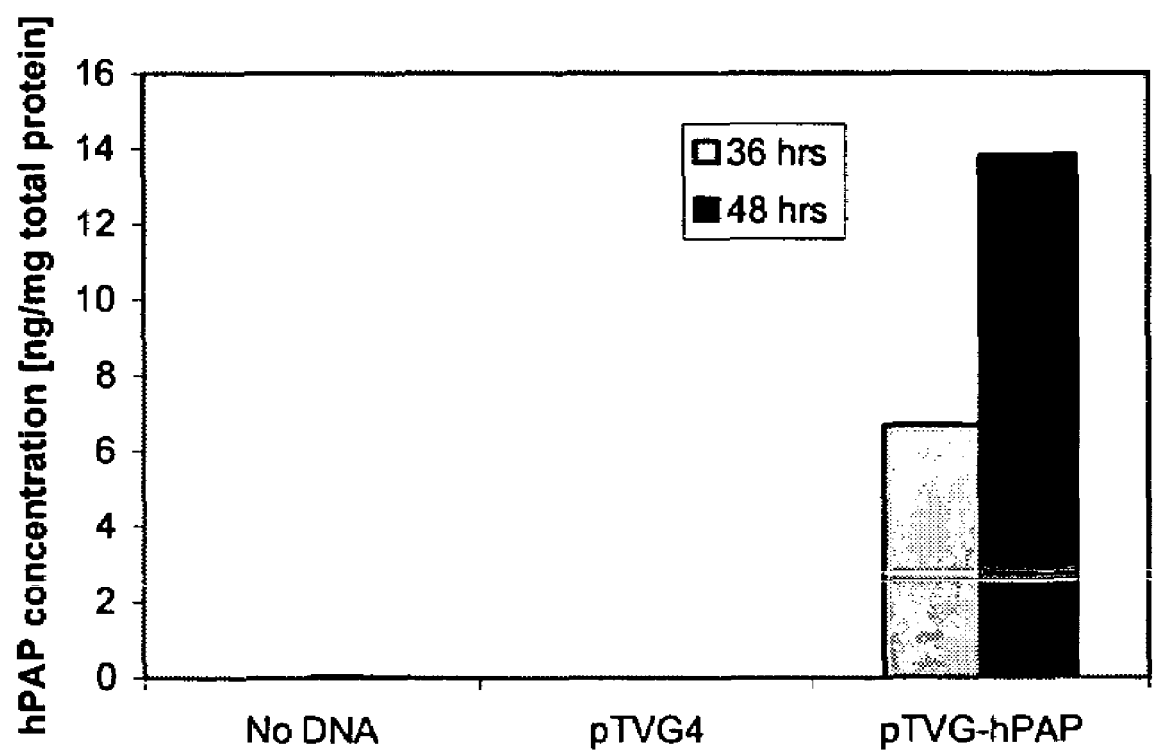
FIG. 5 shows that transfection with PTVG-HP leads to PAP expression in eukaryotic cells. CHO cells were transiently transfected with 1 µg of pTVG4 or pTVG-HP (or no DNA). After 36 and 48 hours, cell lysates were screened by capture ELISA for human PAP.
Figure 6:
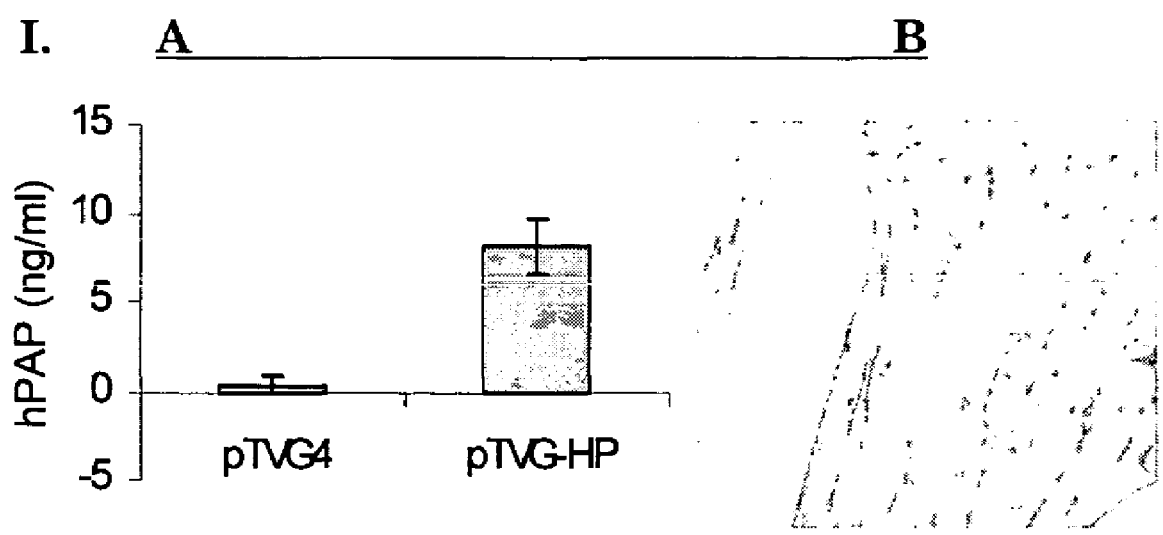
FIG. 6 shows that administration of pTVG-HP intraarterially leads to high levels of antigen expression. Male Lewis rats received 500 µg of control pTVG4 plasmid (n=2) or plasmid expressing hPAP, pTVG-HP (n=2) by intraarterial administration into the external iliac artery. (A) Sera were obtained on day 5 from each animal and analyzed by quantitative capture ELISA for serum hPAP concentrations. (B) Hind limb muscle biopsy obtained from an animal receiving the pTVG-HP intraarterially was stained immunohistochemically for hPAP expression (brown).

The cDNA coding sequence for human PAP has been cloned into this vector to produce the construct pTVG-HP. The pTVG-HP plasmid has been deposited under the Budapest Treaty with the International Depository Authority—American Type Culture Collection—located at 10801 University Blvd. Manassas, Va. 20110-2209, USA on Sep. 21, 2006. The Accession No. for the pTVG-HP plasmid in connection with this deposit is PTA-7893. This is the construct to be used for the clinical trial proposed. With funded support from the NGVL, manufacturing of this DNA under GMP conditions is currently underway. Transient transfection of Chinese Hamster Ovary (CHO) cells followed by capture ELISA have confirmed that PAP is expressed in vitro (FIG. 5). In addition, PAP expression has been shown in an in vivo study as well. Specifically, 500 µg of either pTVG4 or pTVG-HP plasmid DNA was administered to male Lewis rats by direct administration to the right external iliac artery. Sera were obtained 5 days after administration and animals were euthanized after ten days. Sera were then evaluated for PAP protein concentration by capture ELISA, and hind limb muscle biopsies were stained immunohistochemically for PAP expression, as shown in FIG. 6. No PAP expression was detected in muscle tissue from animals receiving the pTVG4 control vector (not shown).

4. Plasmid DNA stimulates antigen-specific T cell responses in vitro

Figure 7:
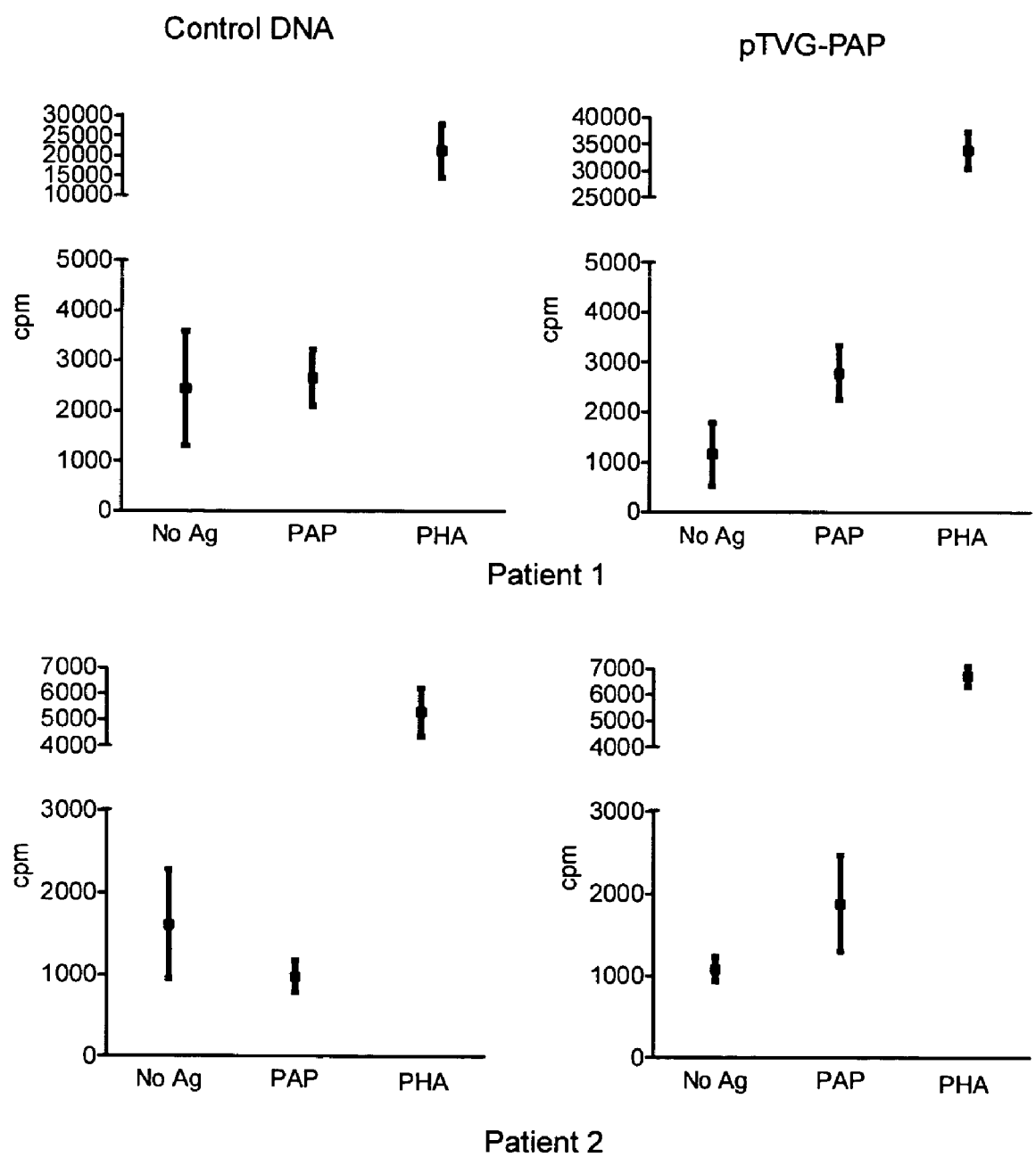
FIG. 7 shows that the pTVG4 vaccine construct encoding rPAP can stimulate hPAP-specific Th responses in vitro. PBMC from two prostate cancer patients were cultured with the pTVG4 construct encoding rPAP or control plasmid. After 3 in vitro stimulations, cultured cells were assayed for proliferative T cell responses to PAP (2 µg/ml), phytohemagglutinin (PHA) (2.5 µg/ml as a positive control), or no antigen, using irradiated autologous PBMC as antigen presenting cells. Shown are the mean and standard deviation of 3H-thymidine uptake in 4-well replicate wells with each antigen. The panels on the left are results from PBMC cultured with control plasmid, and the panels on the right are results from PBMC from the same patients cultured with the vaccine construct.

Cryopreserved peripheral blood mononuclear cells (PBMC) from two patients with metastatic prostate cancer were thawed and re-suspended at 106 cells/ml in RPMI medium (Gibco BRL, Rockville, Md.) supplemented with 10 mM L-glutamine, 2% penicillin/streptomycin, 50 µM β-mercaptoethanol and 10% human AB serum (Valley Biomedical, Winchester, Va.), as well as 2 µg/ml of a plasmid DNA construct encoding the rat PAP protein (pTVG-RP, containing the cDNA for rat PAP in place of the human PAP cDNA) or the vector control plasmid containing no cDNA insert, pTVG4. Proliferating lymphocytes were twice re-stimulated at 7–10 day intervals with irradiated (3300 cGy) autologous PBMC and pulsed with DNA at 2 µg/ml. Media was exchanged every 3–4 days after stimulation with the T cell medium described above containing 10 U/ml rhIL-2 (Chiron, Emeryville, Calif.). After 3 in vitro stimulations, cultured T cells were assayed for proliferative T cell responses to PAP (2 µg/ml), PHA (2.5 µg/ml as a positive control), or no antigen, using irradiated autologous PBMC as antigen presenting cells, as previously described (McNeel et al., 2001, Cancer Res. 61:5161–5167). Shown in FIG. 7 are the mean and standard deviation of 3H-thymidine uptake in 4-well replicate wells with each antigen. The panels on the left are results from PBMC cultured with control plasmid, and the panels on the right are results from PBMC from the same patients cultured with the vaccine construct.

Figure 8:
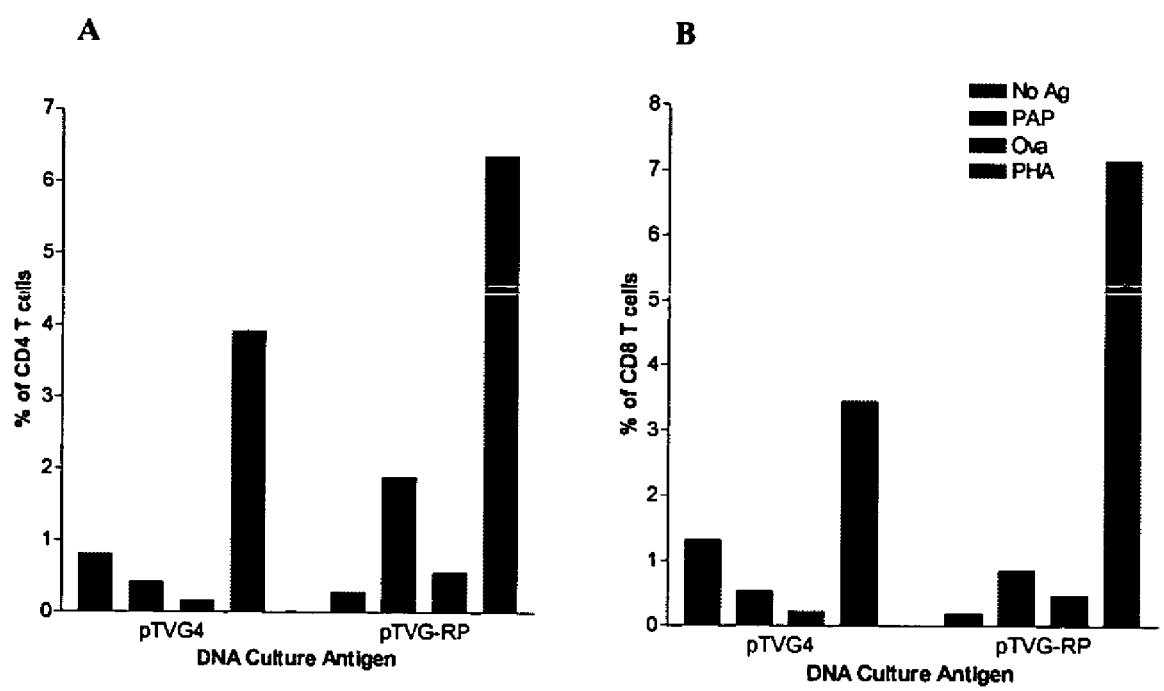
FIG. 8 shows that dendritic cells from patients with prostate cancer can be stimulated in vitro with pTVG-RP to elicit hPAP-specific T cell responses. Immature dendritic cells were grown in vitro from the PBMC of a patient with metastatic prostate cancer. These cells were pulsed with pTVG4 or pTVG-RP, matured with TNFα, and used as antigen presenting cells in a primary T cell culture. After a second in vitro stimulation with DNA-pulsed dendritic cells, the cultures were assessed for antigen-specific T cell proliferation using as test antigens 2 µg/ml hPAP protein, 2 µg/ml ovalbumin (negative control), no antigen, or PHA. Shown are percentage of CD4 (panel A) and CD8 (panel B) subsets proliferating in response to antigen stimulation (BrdU+).

FIG. 7 demonstrates that for both of these patients, low-level PAP-specific proliferative T cell responses could be detected after 3 in vitro stimulations with the vaccine DNA construct encoding rPAP. Similarly, PBMC from another patient with metastatic prostate cancer were allowed to adhere to tissue culture flasks, and adherent cells were cultured in Aim V medium (Gibco) supplemented with GM-CSF and IL-4. After 6 days, the cultured dendritic cells were pulsed with 10 µg/ml pTVG4 or pTVG-RP and 10 U/ml TNFα. Fresh PBMC were then added at a 10:1 effector:APC ratio, cultured for 7 days, and then re-stimulated with DNA-pulsed dendritic cells, as above. After an additional week, cells were assayed for antigen-specific T cell proliferation. As shown in FIG. 8, both CD4 and CD8 T cells specific for hPAP could be detected following stimulation with DNA encoding rPAP, but not the control plasmid.

Example 3

Lewis Rats Immunized with a Vaccinia Virus Expressing hPAP Develop PAP-specific Cellular Immunity and Prostate Tissue Inflammation 1. Immunization with a vaccinia virus vector Immunization with vaccinia virus expressing hPAP, an immunization method permitting antigen expression in the MHC class I pathway, elicits a CTL/Th1 type of PAP-specific immune response and prostate tissue inflammation (Fong et al., 1997, supra; McNeel and Disis, 1999, supra).

Figure 9A:
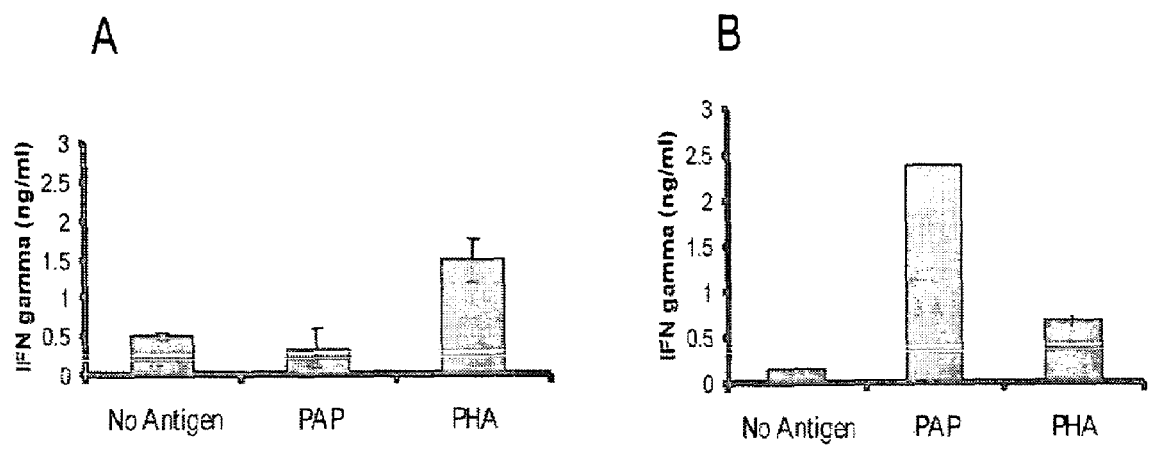
FIGS. 9A and 9B show Lewis rats immunized with vaccinia virus expressing human PAP develop evidence of autoimmune prostatitis.

As shown in FIG. 9A, Lewis rats immunized with vaccinia virus expressing human PAP develop evidence of autoimmune prostatitis. Lewis rats were immunized subcutaneously on day 1 with 2×10⁷ pfu of vaccinia virus expressing PAP and then boosted on day 15 with either recombinant vaccinia virus (panel A), or 25 µg purified PAP administered s.c. in CFA adjuvant (panel B). Splenocytes from immunized animals were cultured for 96 hours in the presence of 2.0 µg/ml human PAP, 2.5 µg/ml PHA, or no antigen. Culture supernatants were then assayed for IFNγ concentration by quantitative ELISA. This figure shows IFNγ concentration for a control experimental animal that did not develop prostatitis (panel A), and one which did (panel B).

Figure 9B:
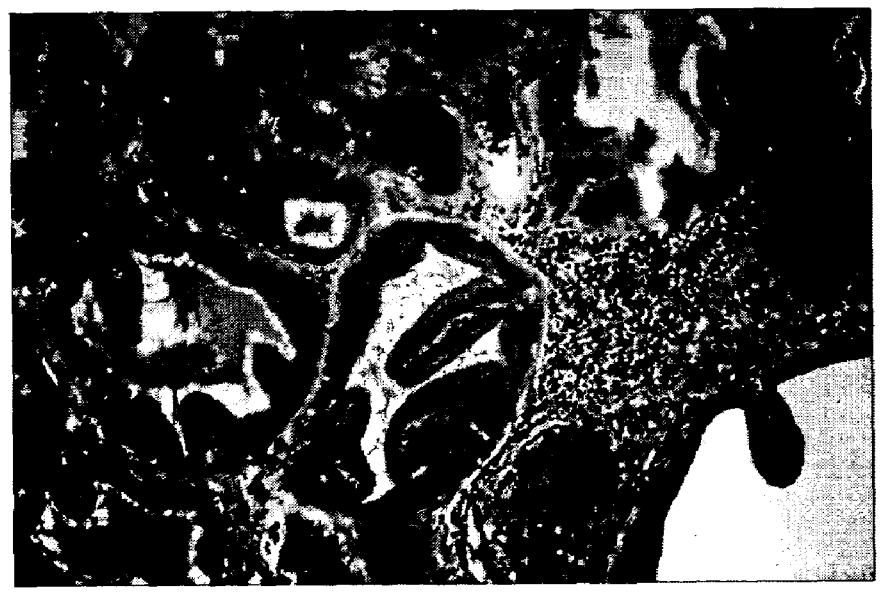

The animals were sacrificed 8 weeks later on day 57. FIG. 9B shows a prostate biopsy stained with hematoxylin and eosin.

Figure 10:
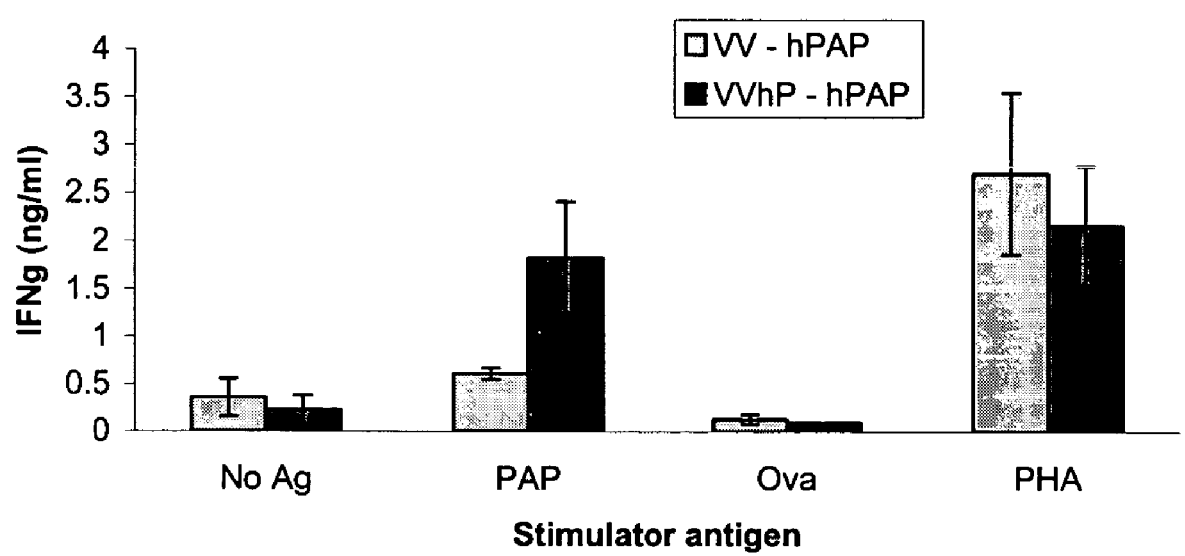
FIG. 10 shows that Lewis rats immunized with vaccinia virus expressing human PAP develop a Th1-type immune response. Lewis rats were immunized subcutaneously on day 1 with $2 \times 10^7$ pfu of either wild type vaccinia virus or recombinant virus expressing PAP and then boosted on day 15 with 25 µg purified PAP administered s.c. in complete Freund's adjuvant. Splenocytes from immunized animals were cultured for 96 hours in the presence of 2.0 µg/ml human PAP, 2.5 µg/ml PHA, 2.0 µg/ml ovalbumin, or no antigen. Culture supernatants were then assayed for IFNγ concentration by quantitative capture ELISA.
Figure 11:
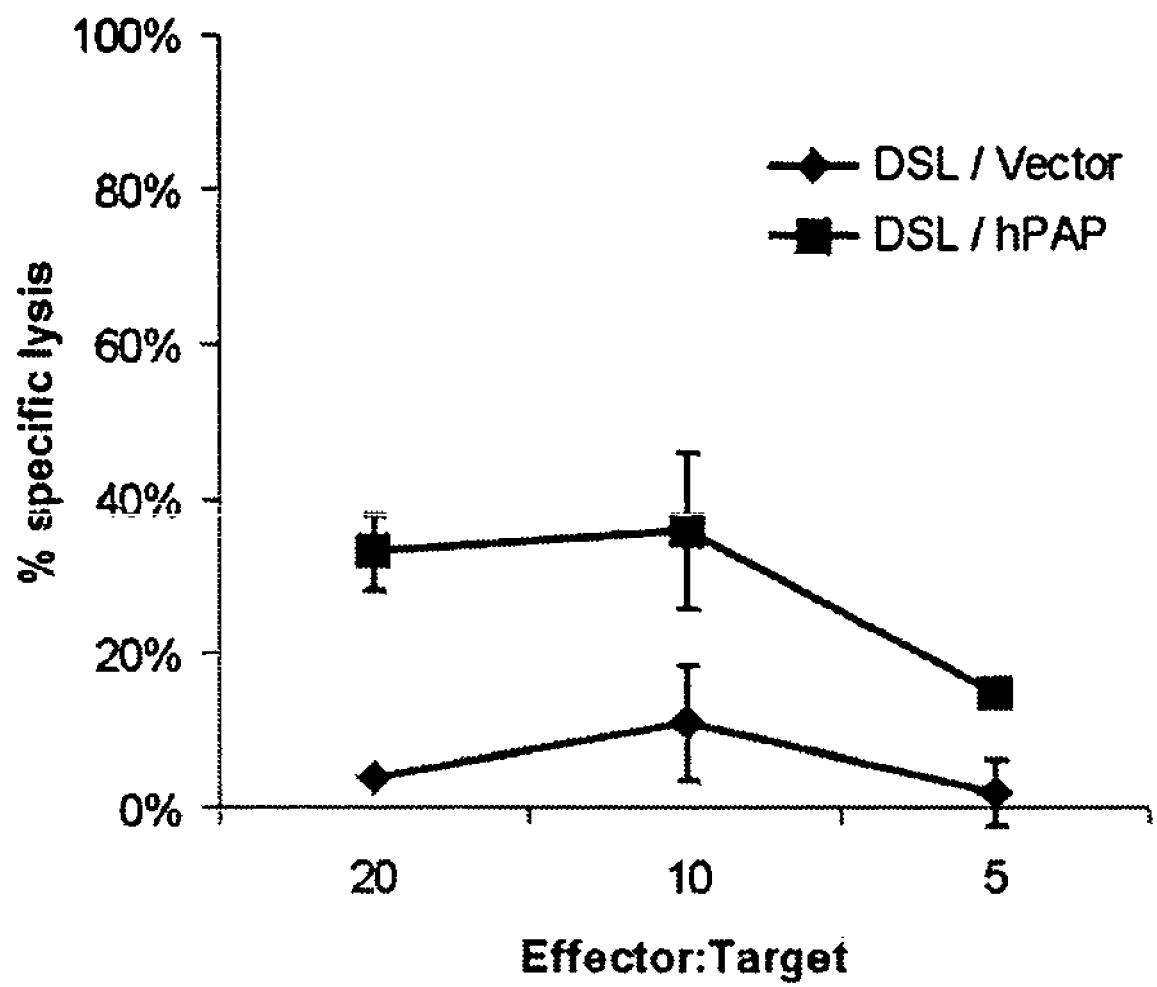
FIG. 11 shows that Lewis rats immunized with vaccinia virus expressing human PAP develop hPAP-specific CTL. Lewis rats were immunized twice at 2-week intervals subcutaneously with $2 \times 10^7$ pfu of vaccinia virus expressing PAP. Splenocytes from immunized animals were assessed after one in vitro stimulation for cytolytic activity using LDH release as indicative of cell lysis (CytoTox 96, Promega).

Antigen-specific secretion of IFNγ was also detected, consistent with a Th1-type of response (FIG. 10). In addition, CTL responses could be detected using a target syngeneic cell line (DSL) expressing hPAP (FIG. 11).

Example 4

Figure 12:
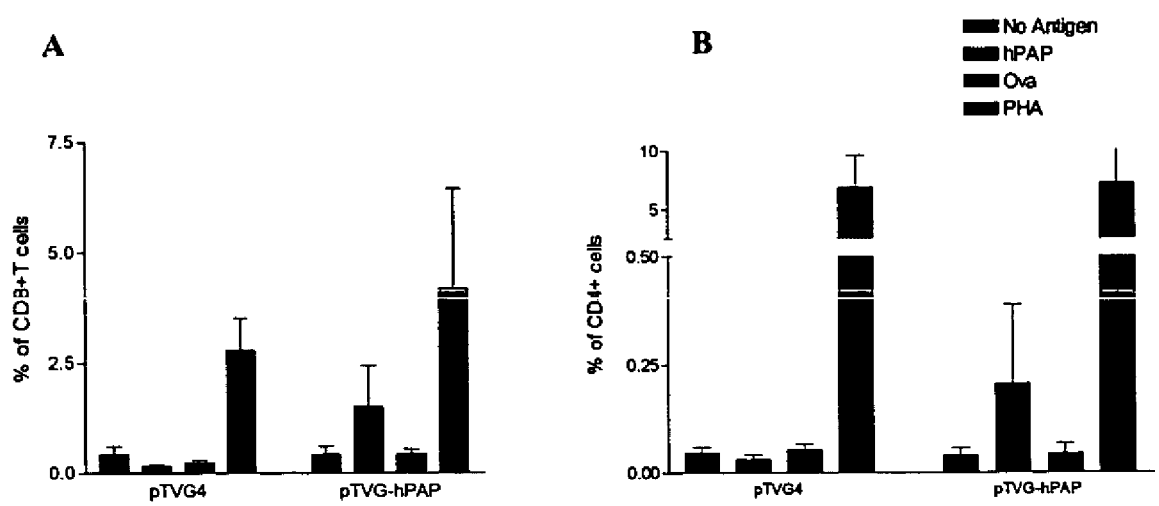
FIG. 12 shows that Lewis rats immunized with pTVG-HP develop PAP-specific cellular immunity. Animals were immunized as described, and euthanized with collection of spleens 14 days after the 2nd immunization. Splenocytes cultures were co-cultured as described above with hPAP protein (2 µg/ml), ovalbumin (2 µg/ml), PHA as a positive mitogen control, or no antigen. After 72 hours, cells were pulsed with BrdU, and analyzed by flow cytometry for CD4 or CD8 surface expression and BrdU uptake. Shown are the percentage of total CD8 (panel A) or CD4 (panel B) T cells staining positive for BrdU (BD Pharmingen kit). Data show the mean and standard deviation for three animals in each group.
Figure 14:
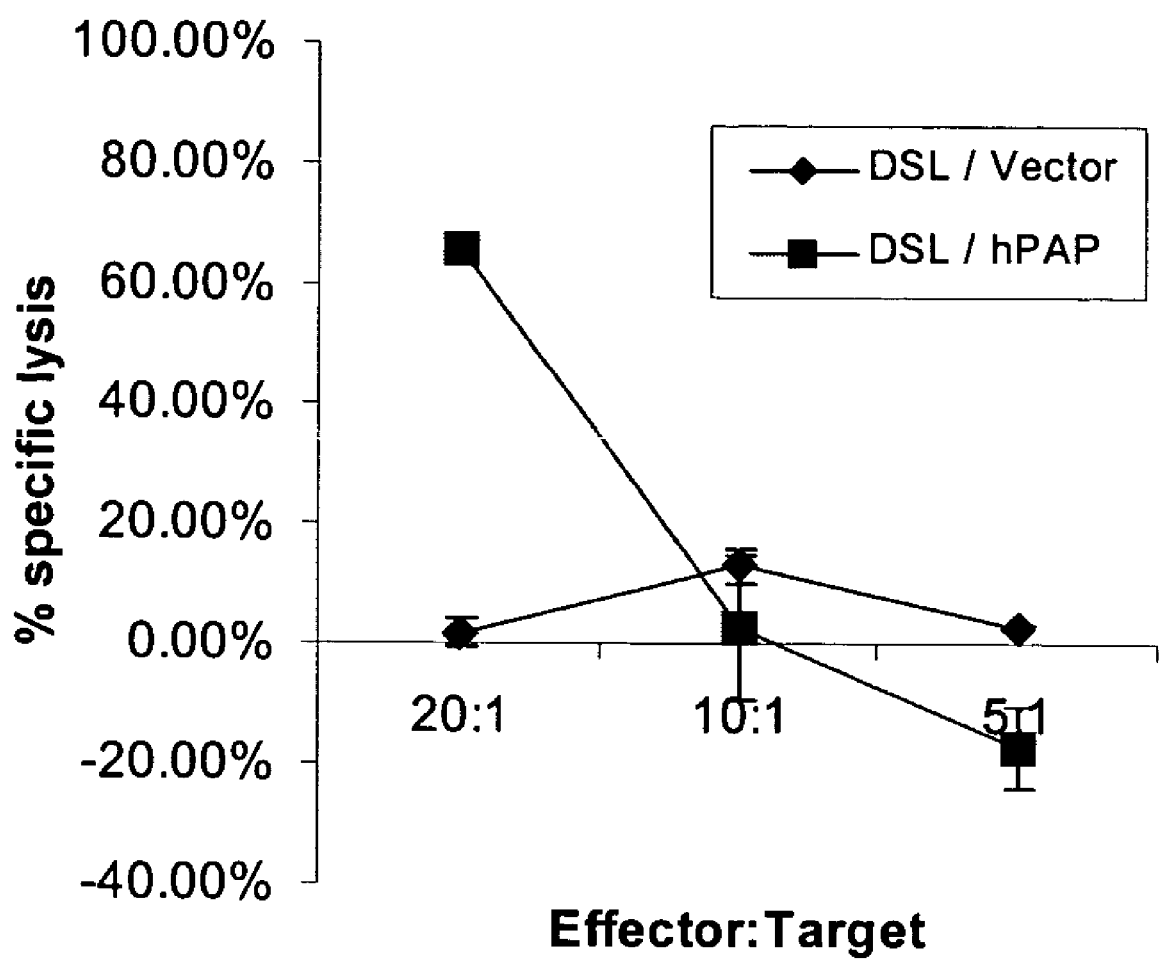
FIG. 14 shows that immunization of male Lewis rats with pTVG-HP elicits PAP-specific CTL. Splenocytes from immunized animals were taken through one week in vitro stimulation with irradiated syngeneic stimulator cells expressing hPAP. Cytotoxicity was then tested using target syngeneic DSL cell lines tranfected with pTracer (DSL/Vector) or pTr-hPAP expressing hPAP (DSL/hPAP). Cytotoxicity was measured by release of lactate dehydrogenase after 9 hours (Promega, Cytotox 96 assay kit). Results were analyzed as for standard chromium release assay and the figure shows the mean and standard deviation for triplicate samples.
Figure 16:
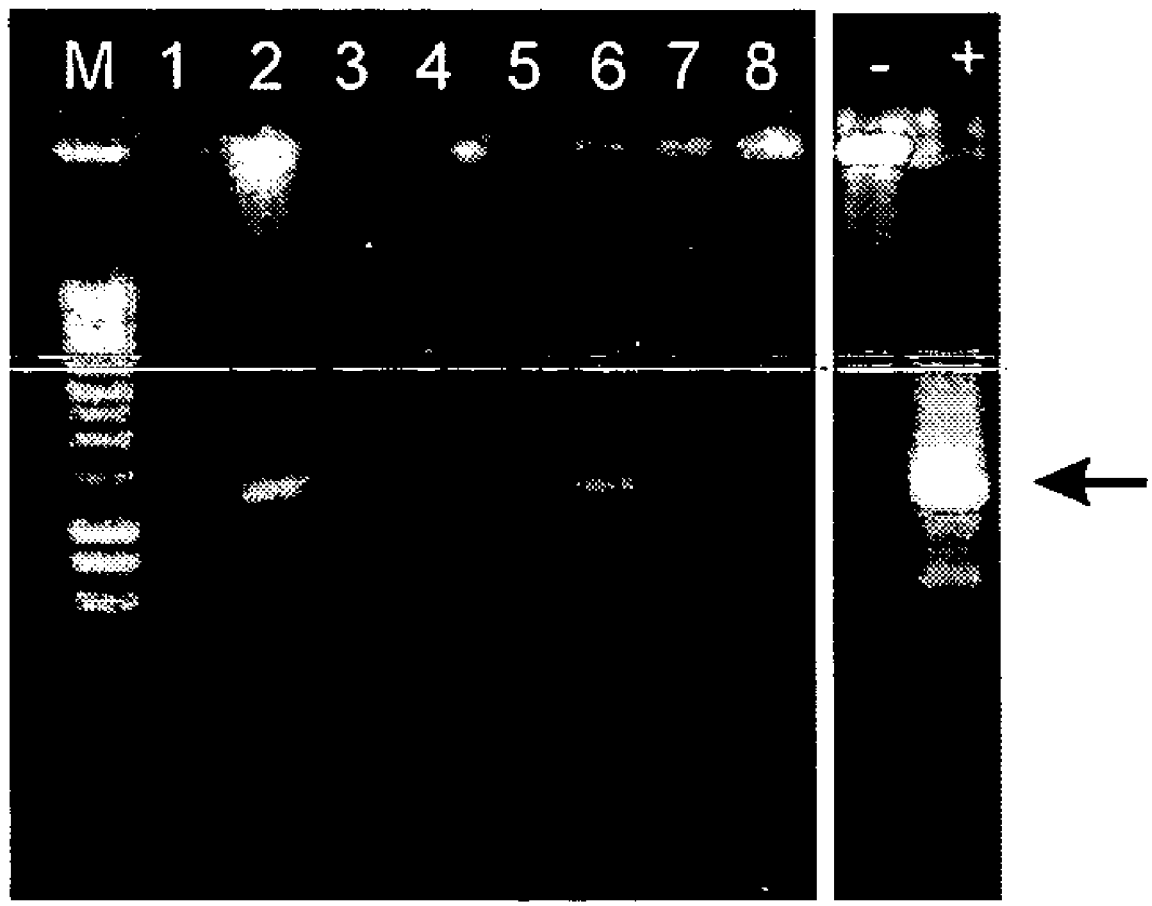
FIG. 16 shows that plasmid DNA used for immunization can be detected at the site of immunization at least 2 weeks after vaccination in at least three of the eight immunized rodents.

Lewis Rats Immunized with pTVG-HP Develop PAP-specific Cellular Immunity and Prostate Tissue Inflammation 2–3 month-old male Lewis rats were immunized intradermally with 100 µg of plasmid DNA and 5 µg murine GM-CSF protein as an adjuvant. Immunization was repeated in 2 weeks, and animals were sacrificed two weeks after the boost. Rodents immunized with pTVG-HP, but not the pTVG4 control vector, developed a proliferative CD4 and CD8 T cell response to human PAP (FIG. 12). Analysis of IFNγ and IL-10 secretion in response to antigen stimulation demonstrated this to be predominantly IFNγ-secreting, consistent with a Th1-type response (not shown). In addition, animals receiving pTVG-HP as a vaccine developed a detectable antibody response to PAP that was predominantly IgG2b in subtype, compared with animals immunized with PAP protein in Freund's adjuvant, the latter animals developing primarily an IgG1-specific response (FIG. 13). Moreover, cytotoxic T cell (CTL) responses specific for PAP could be detected after one in vitro stimulation to a syngeneic Lewis rat pancreatic cell line, DSL, expressing hPAP in pTVG-HP immunized animals (FIG. 14). CTL responses specific for PAP could not be detected in any control animals (data not shown). Finally, some animals receiving the pTVG-HP vaccine developed prostate tissue inflammation, suggesting the development of a cross-reactive immune response to tissue expressing rPAP (see FIG. 15 and Example 7 below). Again, no prostate tissue inflammation was observed in control animals (data not shown). Skin obtained from the site of immunization at the time of necropsy was digested, and the nucleic acids were precipitated. This was then tested by PCR for the presence of immunizing plasmid DNA. FIG. 16 demonstrates that plasmid-specific DNA could be detected in 3/8 animals even two weeks after immunization, suggesting that plasmid DNA may persist, providing a long-lived source of antigen expression.

Example 5

Figure 17:
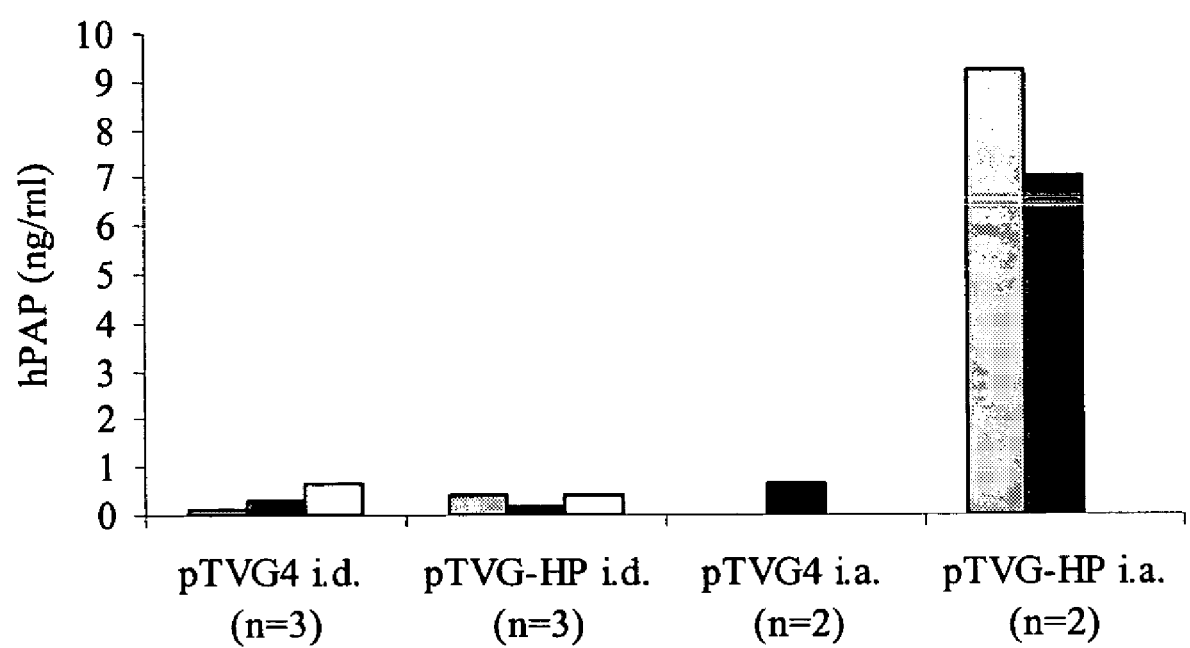
FIG. 17 depicts that administration of plasmid DNA encoding PAP intraarterially leads to high levels of antigen expression.

Administration of Plasmid DNA Encoding PAP Intraarterially Leads to High Levels of Antigen Expression Male Lewis rats received 500 µg of control pTVG4 plasmid or plasmid expressing hPAP, pTVG-HP, by either intradermal administration (n=3) or intraarterial administration into the external iliac artery (n=2). Sera was obtained on day 5 from each animal and analyzed by quantitative capture ELISA for serum hPAP concentrations. As shown in FIG. 17, administration of plasmid DNA encoding PAP intraarterially leads to high levels of antigen expression.

Example 6

Plasmid DNA Used for Immunization can be Detected at the Site of Immunization at Least 2 Weeks After Vaccination Lewis rats were immunized intradermally on days 1 and 15 with 50 µg of plasmid DNA. Two weeks after the second immunization, animals were sacrificed and biopsies taken from the site of immunization. Samples were treated overnight with proteinase K, and the nucleic acids precipitated with ethanol. Detection of plasmid DNA was done by PCR using plasmid-specific primers. Lane M is a DNA size marker; lanes 1–8 are individual animal biopsies tested; lanes + and − are control plasmids. FIG. 16 shows that plasmid DNA used for immunization can be detected at the site of immunization at least 2 weeks after vaccination. The arrow indicates the size of the expected band.

Example 7

Rat Immunization with a Plasmid DNA Vaccine

Immunization with a plasmid DNA vaccine encoding the hPAP xenoantigen was further shown to elicit prostate-tissue inflammation, and male rats immunized with plasmid DNA expressing hPAP under a eukaryotic promoter develop evidence of autoimmune prostatitis. Specifically, the cDNA for hPAP was cloned into the eukaryotic expression vector pCDNA3.1 (Invitrogen Corp., Carlsbad, Calif.), and expression of protein was confirmed by transient transfection experiments of a Chinese hamster ovary (CHO) cell line (see above). Two- to three-month-old male Lewis rats were then immunized intradermally with 50 µg of plasmid DNA with 20 µg murine granulocyte macrophage colony stimulating factor Granulocyte Macrophage Colony Stimulating Factor (GM-CSF) as a vaccine adjuvant twice at 2-week intervals. Rodents immunized with plasmid DNA encoding hPAP, but not the pCDNA3.1 vector, developed a low-level proliferative T cell response and antibody response to hPAP (data not shown). Two weeks after the 2nd immunization animals were sacrificed and prostate biopsies obtained. The figure shows biopsies stained with hematoxylin and eosin. As shown in FIG. 15, two out of three rats immunized with plasmid DNA encoding hPAP (panel B), but not the control vector (panel A), developed marked prostate inflammation with areas of glandular destruction. (to be incorporated with prior discussion of FIG. 15).

Similar results have been found with other plasmid constructs expressing hPAP from a strong eukaryotic promoter (not shown).

In a different experiment, groups of six 2-month old Lewis rats are immunized twice at 2-week intervals as described above, using 50, 100, or 500 µg of pTVG-HP or 500 µg control vector pTVG4 with 5 µg murine GM-CSF as a vaccine adjuvant. Immunizations are performed intradermally in a 100 µl total volume of normal saline. Other groups of six male Lewis rats receive 50, 100, 500 or 1500 µg pTVG-HP DNA, or 1500 µg control pTVG4, suspended in 10 ml of normal saline, and administered once by rapid injection intraarterially in the hind limbs, as previously described (Budker, et al., 1998, Gene Ther. 5:272–276). Blood is drawn from the tail vein 48 hours and 5 days after each immunization, or intraarterial administration, for serum PAP levels as described above. Animals are sacrificed two weeks after the second immunization or intraarterial administration with collection of blood, spleens, prostate tissue biopsy, and hind limb muscle biopsy. This study is performed in two sets at different times with nine groups of three animals per group. Immunological responses are assessed, evaluating PAP-specific antibody responses, cytokine-secreting T cell responses by ELISPOT, CD4 and CD8 antigen-specific T cell proliferation, and assays of antigen-specific cytotoxic T cells. Direct immunohistochemical evaluation of PAP expression and inflammation is with the hind limb muscle biopsies and prostate tissue. Peptide-specific T cells are also assessed as described above, to determine the peptide epitopes presented by DNA administered by the intraarterial route compared with the intradermal route of delivery.

Immunological evaluation and statistical analysis are performed according to the procedures described in Example 10, infra. The primary measure of response for these studies is prostatitis score. In the first set of experiments, there are 9 treatment groups: control and three doses for i.d. delivery and control and four doses for intraarterial delivery. In the second set of experiments, there are five treatment groups: one control group, and four groups receiving intraarterial delivery followed by intradermal delivery. As before, a group size of 6 animals (54 for the first experiments and 30 for the second experiments) provides 90% power to detect changes in average prostatitis score ranging from 0.2 for control animals to 2.5 for the highest intravascular dose.

Example 8

Administration of Plasmid DNA Encoding PAP Intravenally Leads to High Level of Antigen Expression in Hepatocytes The plasmid vectors of the present invention may be delivered to the patient in need thereof intravascularly. Intravascular delivery may be by direct peripheral artery or venous delivery, or by visceral arterial or venous infusion, such as by direct delivery to the hepatic artery, using well established methods known to those with ordinary skills in the art. Intravenous delivery may be by tail vein injection, when appropriate. This delivery leads to a high level of antigen expression in hepatocytes. Expression of the antigen in liver, a tissue more rich with antigen-presenting cells, may lead to a more pronounced Th1/CTL response than expression in muscle tissue.

Example 9

Figure 18:
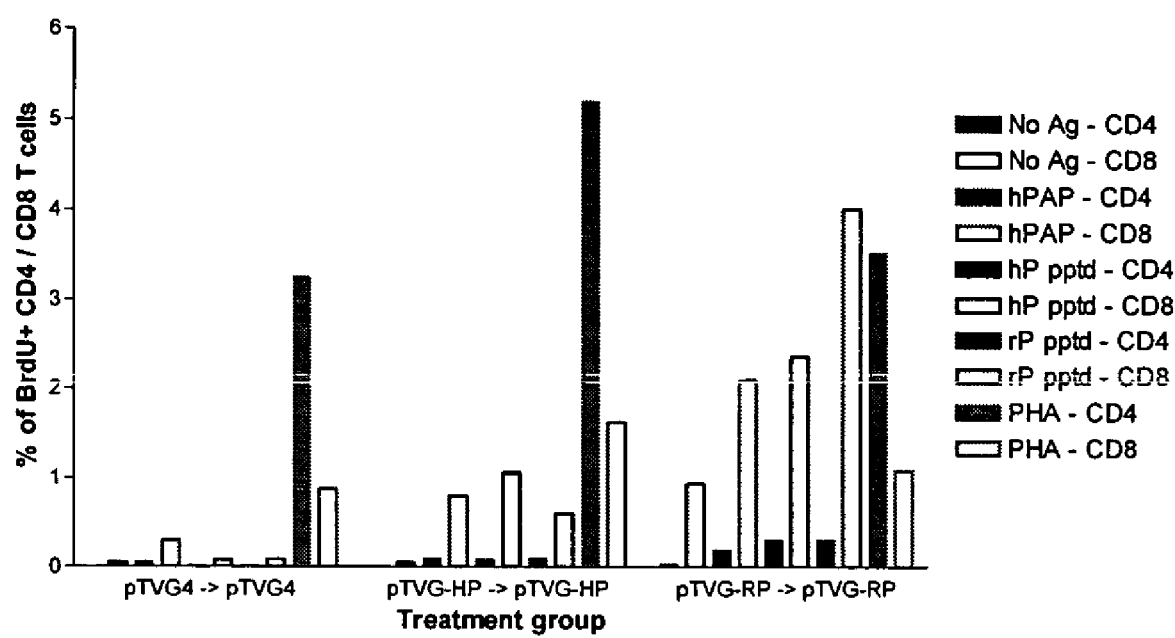
FIG. 18 shows that immunization of male Lewis rats with plasmid DNA vaccines elicits T cell immune responses cross-reactive with the xenoantigen. Male Lewis rats were immunized twice 14 days apart with either pTVG4 control, pTVG-HP, or pTVG-RP. 14 days after the final immunization, splenocytes were assessed for antigen-specific T cell proliferation in the presence of no antigen (red), 2 μg/ml hPAP protein (green), 10 μg/ml peptide pool derived from hPAP (blue), 10 μg/ml peptide pool derived from rPAP (purple), or PHA (positive control, orange). Shown are the percentage of CD4 and CD8 subsets proliferating in response to antigen stimulation (BrdU+). (hP pptd=hPAP-derived peptide pool, rP pptd=rPAP-derived peptide pool)

Immunization of Male Lewis Rats with Plasmid DNA Vaccines Elicits T Cell Immune Responses Cross-reactive with the Xenoantigen 2–3 month-old male Lewis rats were immunized intradermally with 100 µg pTVG4, pTVG-HP, or pTVG-RP and 5 µg murine GM-CSF (mGM-CSF) adjuvant twice, as described above. 14 days after the second immunization, animals were euthanized and assessed for T cell proliferative responses after culture with media only (no antigen), 2 µg/ml purified hPAP protein, to a pool of three 15-mer peptides (p199, p228 and p351) derived from (and specific for) hPAP, a pool of four 15-mer peptides (p44, p198, p227, and p350) derived from (and specific for) rPAP, or PHA as a positive control. As shown in FIG. 18, the control treated animal did not develop hPAP protein or PAP-derived peptide-specific responses. The animal treated with pTVG-HP developed hPAP-specific CD4 and CD8 T cells, as well as peptides derived from hPAP, and to a lesser extent the peptides derived from rPAP. The animal treated with pTVG-RP developed rPAP peptide-specific T cell responses, as well as a response to the hPAP protein and hPAP-specific peptides. In addition, some animals immunized with pTVG-HP, but not pTVG4, developed prostate tissue inflammation and glandular architecture destruction, further demonstrating a cross-reactive immune response recognizing rPAP.

Example 10

Xenoantigen Priming Followed by Boosting with Autoantigen or Xenoantigen

The DNA vaccines of the present invention are preferably used in a prime-boost strategy to induce robust and long-lasting immune response to PAP.

1. Vectors and Immunization Procedures

A plasmid vector pTVG4, a derivative of pNGVL3, a plasmid designed for DNA immunization and obtained from the National Gene Vector Laboratories at the University of Michigan was constructed. The plasmid pTVG-HP contains the cDNA for hPAP downstream of a CMV promoter, and the plasmid pTVG-RP contains the cDNA for rPAP downstream of the CMV promoter in place of the hPAP cDNA, both within the pTVG4 vector.

Groups of six 2–3 month old male Lewis rats are immunized with 100 µg of plasmid DNA encoding hPAP (pTVG-HP), rPAP (pTVG-RP), or the parental control plasmid pTVG4. Immunization is performed as previously described, intradermally in the ear pinna, with 5 µg of murine GM-CSF as a vaccine adjuvant. After 2 weeks, immunizations are boosted with 100 µg of plasmid DNA encoding the same protein or the homologue. Control animals receive booster immunization with the vector alone. Animals are sacrificed two weeks after the booster immunization with collection of sera, spleens, and prostate tissue.

A second set of experiments explore different prime-boost strategies. Specifically, groups of 2–3 month-old male Lewis rats receive 500 µg of either pTVG-HP or pTVG-RP by rapid intraarterial delivery as described above. Two weeks later, animals receive either the hPAP- or rPAP-encoding plasmid administered intradermally. A control group receives the pTVG4 plasmid by both delivery methods. Animals are sacrificed two week after the booster immunization with collection of blood and spleens for immunological analysis, and prostate and hind limb muscle tissue biopsies for immunohistochemical analysis.

Immunological analysis is performed as described above, with analysis of the peptide-specific T cell epitopes recognized. These experiments test not only the ability of a xenoantigen to prime a response to the native antigen, but also determine if an intradermal booster immunization is effective in augmenting the immunity elicited by intraarterial administration of plasmid DNA.

2. Immunological evaluation:

Humoral immune responses to hPAP and rPAP are quantitatively evaluated in experimental animals using an indirect ELISA method. Specifically, the cDNAs for hPAP and rPAP have been previously cloned into the pCDNA4/His-Max expression construct (Invitrogen) in such a fashion to generate a polyhistidine epitope tag at the amino terminus of each gene product. Capture ELISAs are performed as previously described (McNeel et al., 2001, Proc. Amer. Assoc. Cancer Res. 42:156) using a monoclonal antibody specific for the polyhistidine tag to capture either the human or rat antigen from CHO cells transfected to express these proteins. Rat sera are then used to screen for anti-PAP specific responses, with antibodies detected by anti-rat Ig secondary antibodies, again as previously described (McNeel, et al., 2000, J. Urol. 164:1825–1829). IgG subsets are determined using subset-specific secondary antibodies.

Second, T cell responses specific for hPAP or rPAP are evaluated in individual experimental animals by both T cell proliferation and ELISPOT. T cell proliferation is assessed by standard 3H-thymidine incorporation assays or by flow cytometric analysis of BrdU incorporation using a BD Pharmingen kit BD Biosciences (San Diego, Calif.), using either purified PAP protein or stable transfectants of the syngeneic Lewis rat DSL pancreatic cell line expressing either human or rat PAP. ELISPOT is used to assess both IFNγ and IL-4 cytokine secretion in response to antigen stimulation using the same purified protein or PAP-expressing DSL cell lines described. These ELISPOT methods have been described (McNeel et al., 2001, Proc. Amer. Assn. Cancer Res., 42:277; Zou et al., 1999, J. Neuroimmunol. 94:109–121). Specifically, sterile 96-well ELISPOT filter plates (Millipore) are coated with 5 µg/ml capture antibody (IFNγ clone DB1, Harlan; IL-4 clone OX-81, Pharmingen) overnight. About $10^4$ splenocytes from immunized animals are then co-cultured in replicate wells with PAP-expressing irradiated (120 Gy) DSL cell lines, a control transfected DSL cell line, or 40 ng/ml PMA+0.4 µg/ml ionomycin as a positive control. After 48 hours, plates are washed, sequentially probed with secondary antibody (biotinylated anti-IL-4, RDI; polyclonal rabbit anti-rat IFNγ, RDI) and tertiary reagent (streptavidin-conjugated alkaline phosphatase, Bio-Rad; or anti-rabbit IgG conjugated to alkaline phosphatase, Sigma), and then developed with BCIP/NZT substrate (Bio-Rad). Spots are then enumerated with determination of the responder cell frequency per 10,000 splenocytes. A Student's t test is used to compare the number of spots from replicate antigen-stimulated wells with control wells, and between immunized and control animals, to detect significant differences in T cell frequencies.

Finally, cytotoxicity is assessed by both an in vitro assay as well as an in vivo measure by direct immunohistochemical evaluation of prostate biopsies from experimental animals. For the in vitro assays, stable transfectants of the DSL cell line expressing human or rat PAP are used as target cells in standard cytotoxicity assays using effector splenocytes in several effector-to-target ratios. Cytotoxicity is assessed by flow cytometry using propidium iodide staining of fluorescently labeled target cells [Molecular Targets]. In addition, prostate tissue of immunized animals is analyzed histologically for evidence of prostatitis, and graded with respect to the amount of inflammation in a blinded fashion (0: no inflammatory cells; 1: <10 lymphocytes/1 mm field; 2: 10–100 lymphocytes/1 mm field; 3: 100–1000 lymphocytes/1 mm field; 4: >1000 lymphocytes/1 mm field and/or disruption of glandular architecture by inflammation (Zhang et al., 2001, Hum. Gene Ther. 12: 427–438). The presence of CD4 or CD8 T cells and NK cells is evaluated and quantified by immunohistochemistry.

3. Assessment of Prostatitis Scores

The primary measure of immune response in immunized animals is prostatitis score as assessed by histopathology. The scores are defined as follows: 0: no inflammatory cells; 1: <10 lymphocytes/1 mm field; 2: 10–100 lymphocytes/1 mm field; 3: 100–1000 lymphocytes/1 mm field; 4: >1000 lymphocytes/1 mm field and/or disruption of glandular architecture by inflammation. The effect of the immunization method (boosting with xenoantigen versus native antigen) is tested using a generalized linear model assuming a multivariate distribution for ordered categorical data.

4. Statistical analysis

In the first set of experiments, there are five primary treatment groups: control and four prime-boost experimental groups. In the second set of experiments, there are five primary treatment groups: two controls and three experimental groups. A group size of 6 animals (30 rats for the first initial experiments and 24 for the initial second experiments) provides 90% power to detect changes in average prostatitis score ranging from 0.2 for control animals to 2.5 for the highest predicted response. The statistical power is higher for detecting differences between study groups using a continuous evaluation of prostate tissue inflammation as a readout, and/or using the quantitative proliferative and ELISPOT assays. A categorical ranking of prostate inflammation is used as previously described (True et al., 1999, J. Urol. 162:2014–8). A quantitative, continuous evaluation of prostate inflammation by flow cytometric evaluation of numbers of lymphocytes per epithelial cell in prostate biopsies may also be used.

Results from these studies show that plasmid DNA booster immunization with the autologous rPAP primed with the hPAP xenoantigen is more effective than immunization with the xenoantigen alone.

Example 11

Multiple Immunization

Multiple immunizations are also used. Repeated immunization with either the autologous rPAP vaccine or the hPAP vaccine, or in alternating schedules, may be used to produce a strong autoantigen. This is one of the potential advantages of plasmid DNA vaccines over other types of vaccines, such as viral vaccines, in which repeated immunizations are not possible.

Example 12

Clinical Trials

Clinical trials are conducted to test the ability of a plasmid DNA construct encoding hPAP to elicit PAP-specific CD8 T cell responses in subjects with advanced stage prostate cancer. pTVG-HP, a derivative of the pNGVL3 vector

Example 13

Detecting and Monitoring Antigen-specific Immune Responses to PAP in Patients with Prostate Cancer The results below demonstrate that: 1) PAP peptide-specific T cells can be detected by ELISPOT; and 2) dimeric human HLA-A2:Ig can be used to identify peptide-specific CD8 T cells specific for PAP. These methods of analysis will provide the ability to directly monitor the frequency of specific populations of PAP-specific CD8 T cells in HLA-A2 expressing individuals.

1. PAP-specific MHC class I-restricted T cell responses can be detected in patients with prostate cancer by ELISPOT.

Figure 20:
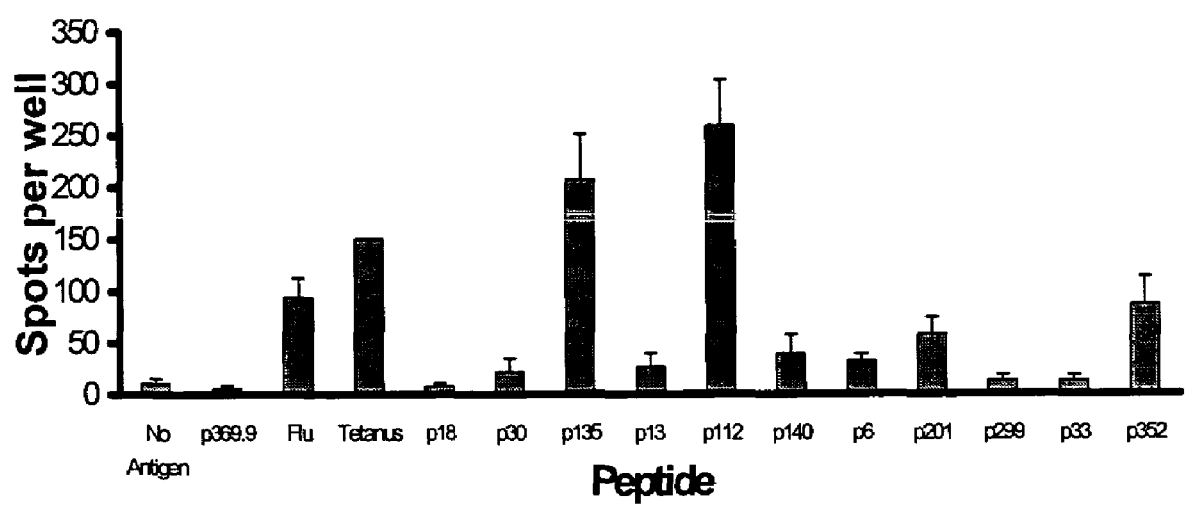
FIG. 20 shows that PAP-specific MHC class I-restricted T cell responses can be detected in patients with prostate cancer by ELISPOT. PBMC from a 58-year-old patient with stage D0 prostate cancer were cultured for 1 week with 10 μg/ml of individual 9-mer peptides, 11 from PAP, p369.9 from HER-2/neu (negative control), influenza peptide and tetanus toxoid protein (positive controls) or no antigen. Cultures were then assayed for antigen-specific IFNγ release upon re-stimulation with antigen for 24 hours in an ELISPOT assay.

Eleven 9-mer oligopeptides were chosen from the amino acid sequence of PAP based on computer modeling and sequence as likely HLA-A2 binding epitopes, and specific for PAP. These peptides were constructed, ranked for HLA-A2 binding by an in vitro T2 assay, and evaluated as stimulator antigens in an IFNγ ELISPOT assay after one in vitro stimulation using the PBMC from a 58-year-old HLA-A2-expressing patient with stage D0 prostate cancer. These results are shown in FIG. 20, with positive controls including a 9-mer HLA-A2 epitope from influenza and tetanus toxoid. These findings demonstrate that individual HLA-A2-binding epitopes from PAP can elicit IFNγ-secreting lymphocytes, and these can be detected in patients with prostate cancer.

Figure 21:
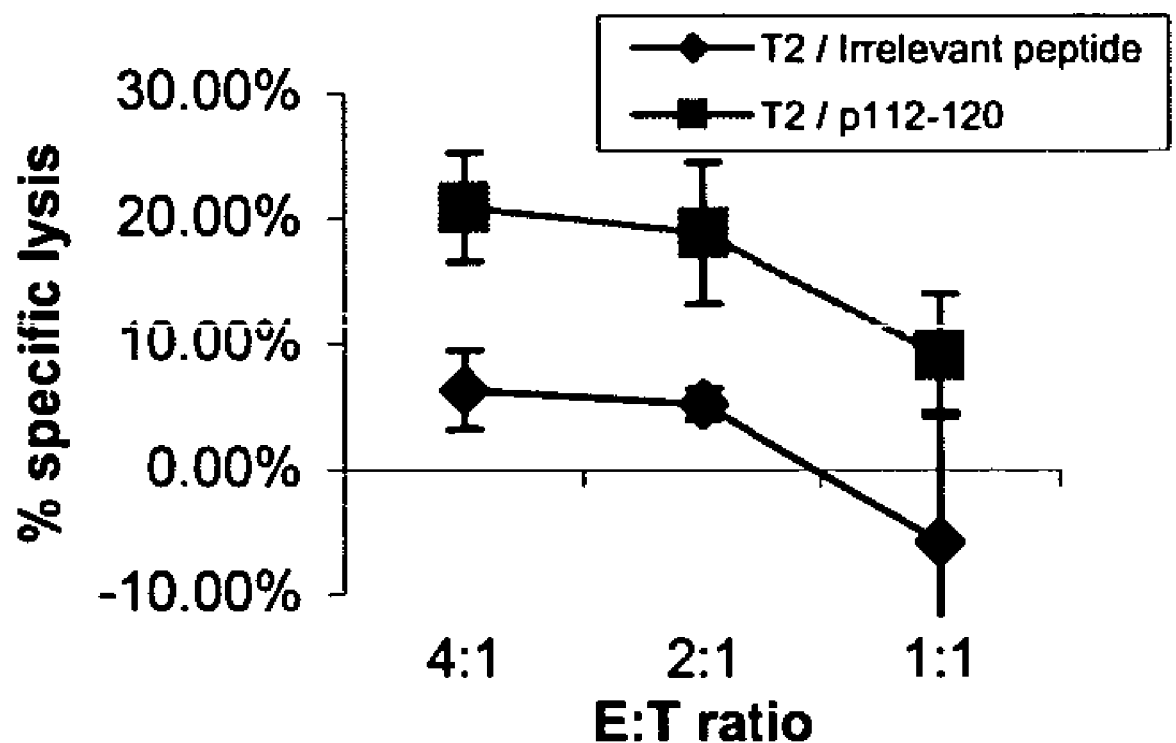
FIG. 21 shows that HLA-A2-specific peptides derived from PAP can be used to stimulate peptide-specific CTL. T cell lines generated after multiple stimulations with p112-120 peptide were assessed for peptide-specific CTL in an LDH release cytotoxicity assay (CytoTox 96, Promega). Lines showed cytotoxicity specific for T2 cells pulsed with the relevant peptide, but not an irrelevant HLA-A2-binding peptide.

Using this methodology and evaluating multiple HLA-A2-positive patients and controls, three novel PAP-specific HLA-A2 epitopes with high affinity for HLA-A2 have been identified, for which peptide-specific T cells could be identified in subjects with prostate cancer (McNeel et al., Identification of PAP-specific MHC class I peptide epitopes by screening patients with prostate cancer by IFN-gamma ELISPOT. (2001) Proc. Amer. Assn. Cancer Res., 42:277). Peptide-specific lines for these identified peptides have been cultured from HLA-A2-positive patients with prostate cancer, with the demonstration of peptide specificity. As an example, the p112-120 nonamer peptide derived from PAP and which showed the greatest reactivity in the assay above, was used as a stimulator antigen in short-term T cell cultures stimulated with autologous GM-CSF and IL-4 generated dendritic cells from an HLA-A2-positive subject with prostate cancer. After several weekly in vitro stimulations with irradiated autologous peptide-pulsed PBMC, cultures were found to be predominantly CD8 by flow cytometric phenotype analysis (not shown) and then evaluated for peptide-specific CTL activity. FIG. 21 illustrates that this line demonstrated peptide-specific CTL activity.

Figure 22:
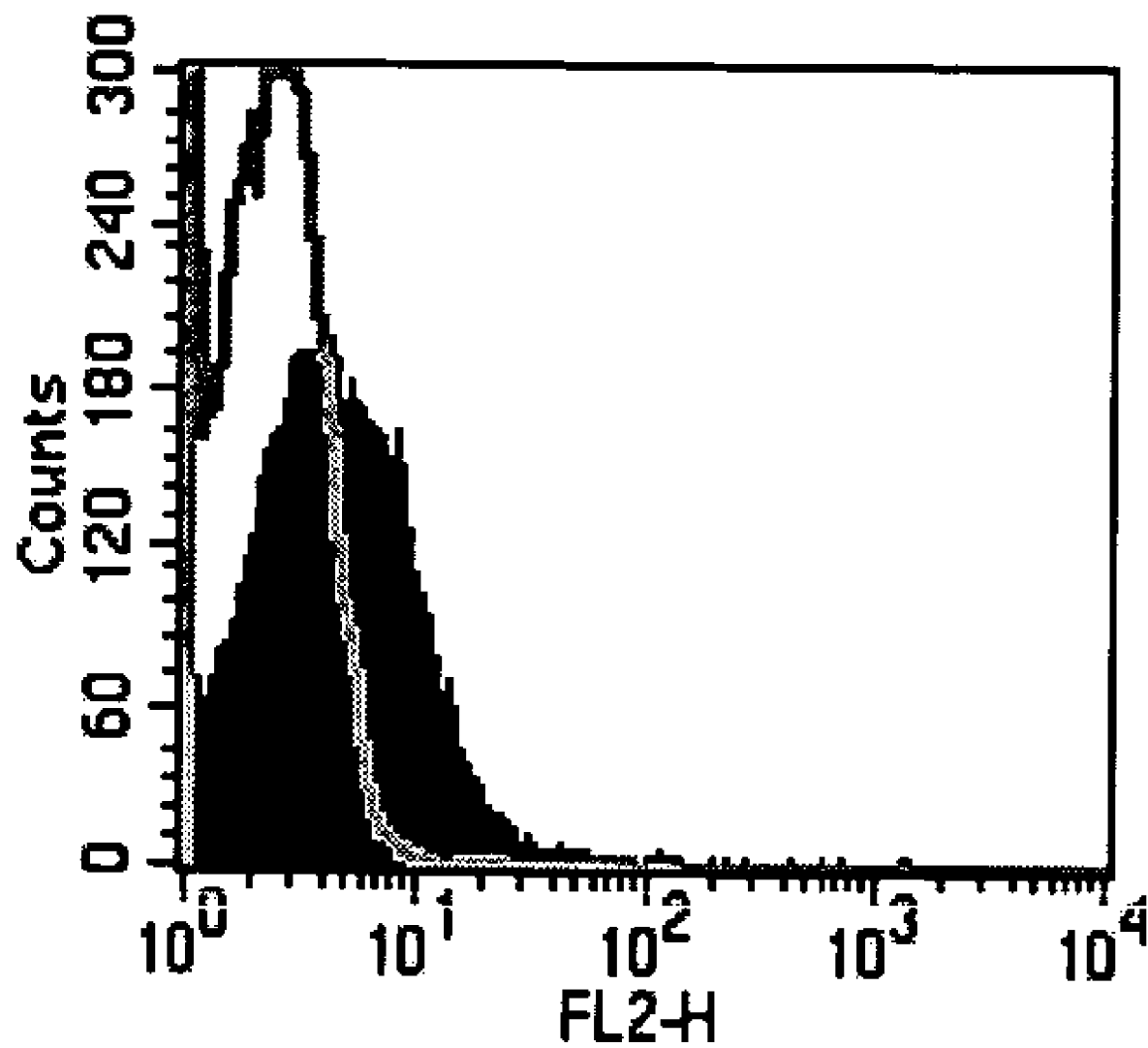
FIG. 22 shows that HLA-A2:Ig dimers can be used to identify peptide-specific CD8 T cells. PAP p112-120 peptide-specific T cell lines were evaluated for peptide-specific T cells using HLA-A2:Ig dimers loaded with an irrelevant HLA-A2-binding peptide (green) or with p112-120 (blue). This figure shows cells gated on CD8+/CD56− expression.

2. Dimeric human HLA-A2:Ig can be used to identify peptide-specific CD8 T cells specific for PAP The ability of soluble MHC molecules fused to IgG to identify and quantify peptide-specific T cells is known (Lebowitz et al., Soluble, high-affinity dimers of T-cell receptors and class II major histocompatibility complexes: biochemical probes for analysis and modulation of immune responses. (1999) Cell Immunol, 192: 175–184). This technology, similar to the tetramer technology, has been successfully applied in multiple systems to identify, activate, or suppress the activity of peptide-specific T cells Dimeric human HLA-A2:Ig loaded with the p112–120 peptide is used to identify peptide-specific CD8 T cells cultured in vitro. FIG. 22 shows an example of a flow cytometric dimer stain of a p112-120 cultured T cell line derived from an HLA-A2-positive subject with prostate cancer.

What is claimed is:

1. A method for inducing a cytotoxic immune reaction to cells expressing human prostatic acid phosphatase (PAP) in a human subject in need thereof, comprising administering intradermally, intramuscularly, intravascularly, intravenously, or intraarterially to the human subject an effective amount of a recombinant DNA plasmid comprising a polynucleotide sequence encoding human PAP, and an immune stimulatory sequence comprising a 5'-GTCGTT-3' motif, wherein the human PAP is expressed and the human subject develops a cytotoxic immune reaction against cells expressing human PAP.

2. The method of claim 1, wherein the human subject has prostate cancer and an antitumor immune response to prostate tumors is elicited in the human subject.

3. The method according to claim 1, wherein destructive prostatitis is induced in the human subject.

4. A DNA vaccine comprising the pTVG-HP plasmid vector.

5. A pharmaceutical composition comprising the DNA vaccine of claim 4, and a pharmaceutically acceptable carrier.

6. A pharmaceutical composition of claim 5, further comprising a suitable amount of GM-CSF.

* * * * *